US009712673B2

(12) United States Patent
Abnett et al.

(10) Patent No.: US 9,712,673 B2
(45) Date of Patent: Jul. 18, 2017

(54) PROVIDING TO A PUBLIC-SAFETY ANSWERING POINT EMERGENCY INFORMATION ASSOCIATED WITH AN EMERGENCY CALL

(71) Applicants: Innacloud Technologies LLC, Worthington, OH (US); Guest Tek Interactive Entertainment Ltd., Calgary (CA)

(72) Inventors: Christopher Abnett, Grove City, OH (US); Russell D. McComb, Delaware, OH (US); Andrew T. MacMillan, Calgary (CA)

(73) Assignees: Innacloud Technologies LLC, Worthington, OH (US); Guest Tek Interactive Entertainment Ltd., Calgary AB (CA)

( * ) Notice: Subject to any disclaimer, the term of this patent is extended or adjusted under 35 U.S.C. 154(b) by 0 days.

(21) Appl. No.: 15/152,423

(22) Filed: May 11, 2016

(65) Prior Publication Data

US 2016/0255197 A1  Sep. 1, 2016

Related U.S. Application Data

(62) Division of application No. 14/557,369, filed on Dec. 1, 2014, now Pat. No. 9,363,373.

(Continued)

(51) Int. Cl.
*H04M 11/00* (2006.01)
*H04M 3/51* (2006.01)

(Continued)

(52) U.S. Cl.
CPC ......... *H04M 3/5116* (2013.01); *A61B 5/0004* (2013.01); *A61B 5/0022* (2013.01);

(Continued)

(58) Field of Classification Search
CPC ........... H04M 3/5116; H04M 3/42068; H04M 7/0024; H04M 3/42323; A61B 5/747;

(Continued)

(56) References Cited

U.S. PATENT DOCUMENTS

| 5,864,755 A | 1/1999 | King et al. |
| 2002/0136361 A1 | 9/2002 | Stumer et al. |

(Continued)

*Primary Examiner* — Stella Woo
(74) *Attorney, Agent, or Firm* — Baker & Hostetler LLP

(57) ABSTRACT

Users store information relevant to first responders in the event of an emergency. When a user later places an emergency call, the user's emergency information is automatically made available to the public-safety answering point operator handling the call. Hotel personal are notified of the call and may listen to and break in to the ongoing call in order to assist. A reverse 9-1-1 broadcast enables hotel personnel to quickly notify guests of an emergency situation via in-room and mobile phones. In the event that police need to conduct surveillance on a target location, the onsite PBX server reconfigures phones within the vicinity of the target location to operate in an open mode and records the audio/visual information received. An incoming call to a hotel room from the PSAP is automatically connected to the in-room phone even if other incoming calls not from the PSAP are being screened by front desk.

13 Claims, 15 Drawing Sheets

Related U.S. Application Data

(60) Provisional application No. 61/910,858, filed on Dec. 2, 2013, provisional application No. 61/952,088, filed on Mar. 12, 2014.

(51) Int. Cl.

| | | |
|---|---|---|
| *G06Q 50/12* | (2012.01) | |
| *H04W 4/16* | (2009.01) | |
| *A61B 5/00* | (2006.01) | |
| *G06F 17/30* | (2006.01) | |
| *H04M 3/42* | (2006.01) | |
| *H04M 7/00* | (2006.01) | |

(52) U.S. Cl.
CPC ........ *A61B 5/747* (2013.01); *G06F 17/30477* (2013.01); *G06Q 50/12* (2013.01); *H04M 3/42068* (2013.01); *H04M 3/42323* (2013.01); *H04M 7/0024* (2013.01); *H04W 4/16* (2013.01)

(58) Field of Classification Search
CPC ................ A61B 5/0022; A61B 5/0004; G06F 17/30477; G06Q 50/12; H04W 4/16
USPC .......................................................... 379/45
See application file for complete search history.

(56) References Cited

U.S. PATENT DOCUMENTS

| | | | |
|---|---|---|---|
| 2003/0012344 A1* | 1/2003 | Agarwal | H04M 11/04 379/37 |
| 2003/0086538 A1 | 5/2003 | Geck et al. | |
| 2003/0148757 A1 | 8/2003 | Meer | |
| 2006/0128357 A1* | 6/2006 | Suryanarayana | H04M 3/42068 455/404.2 |
| 2007/0038476 A1* | 2/2007 | Sternlicht | G06F 19/327 705/2 |
| 2008/0063153 A1 | 3/2008 | Krivorot et al. | |
| 2009/0136006 A1* | 5/2009 | Milton | H04W 76/007 379/45 |
| 2009/0291663 A1* | 11/2009 | Schultz | H04M 3/465 455/404.2 |
| 2010/0262668 A1* | 10/2010 | Piett | H04W 76/007 709/206 |
| 2010/0329443 A1 | 12/2010 | Montaner Gutierrez et al. | |

* cited by examiner

Advanced safety notification (ASN) setup

202 →

| Membership No. | 234-135-876 |
| --- | --- |
| Name | Jonathan Doe |

204 205
[Edit] [Add]

206 → Please enter any personal emergency information that may be relevant in the event of an emergency:

> Medical information:
> 1. Asthma
> 2. Risk of Anaphylaxis
> 3. Allergy to bee stings
> 4. Allergy to penicillin
> 5. Heart disease
> 6. Metal plate in ankle
>
> Medical alert ID: 33-456-224
>
> Emergency contacts:
> Judy Doe: (740) 555-0100 (wife)
> Dr. Candy Lee: (740) 651-9305 (doctor)
> JC Jones: (740) 555-1212 (friend)

208 → Automatically provide your personal emergency information to the public-safety answer point (PSAP) if a call is placed to 9-1-1 from your guest room?

● Yes   ○ No

209 → Automatically provide your personal emergency information to hotel front desk and allow hotel staff to participate in the 9-1-1 call if a call is placed to 9-1-1 from your guest room?

● Yes   ○ No

210 — [Save changes] [Cancel]

FIG. 2

Option 1 - Make emergency information available

1000
— Caller ID for outgoing emergency call to 9-1-1 from guest's room:

| name field                    1000a | # field                          1000b |
|---|---|
| UUID of user ("234-135-876") | DID# for guest room ("740-555-0112") |

1002
— Caller ID for emergency call to 9-1-1 from user's mobile phone:

| name field                    1002a | # field                          1002b |
|---|---|
| UUID of user ("234-135-876") | User's mobile phone # ("740-555-0133") |

Option 2 - Do not make emergency information available

1004
— Caller ID for outgoing emergency call to 9-1-1 from guest's room:

| name field                    1004a | # field                          1004b |
|---|---|
| Guest name ("Jonathan Doe") | DID# for guest room ("740-555-0112") |

1006
— Caller ID for (non-personal) emergency call to 9-1-1 from user's mobile phone:

| name field                    1006a | # field                          1006b |
|---|---|
| Guest name ("Jonathan Doe") | User's mobile phone # ("740-555-0133") |

FIG. 10 by onsite PBX server

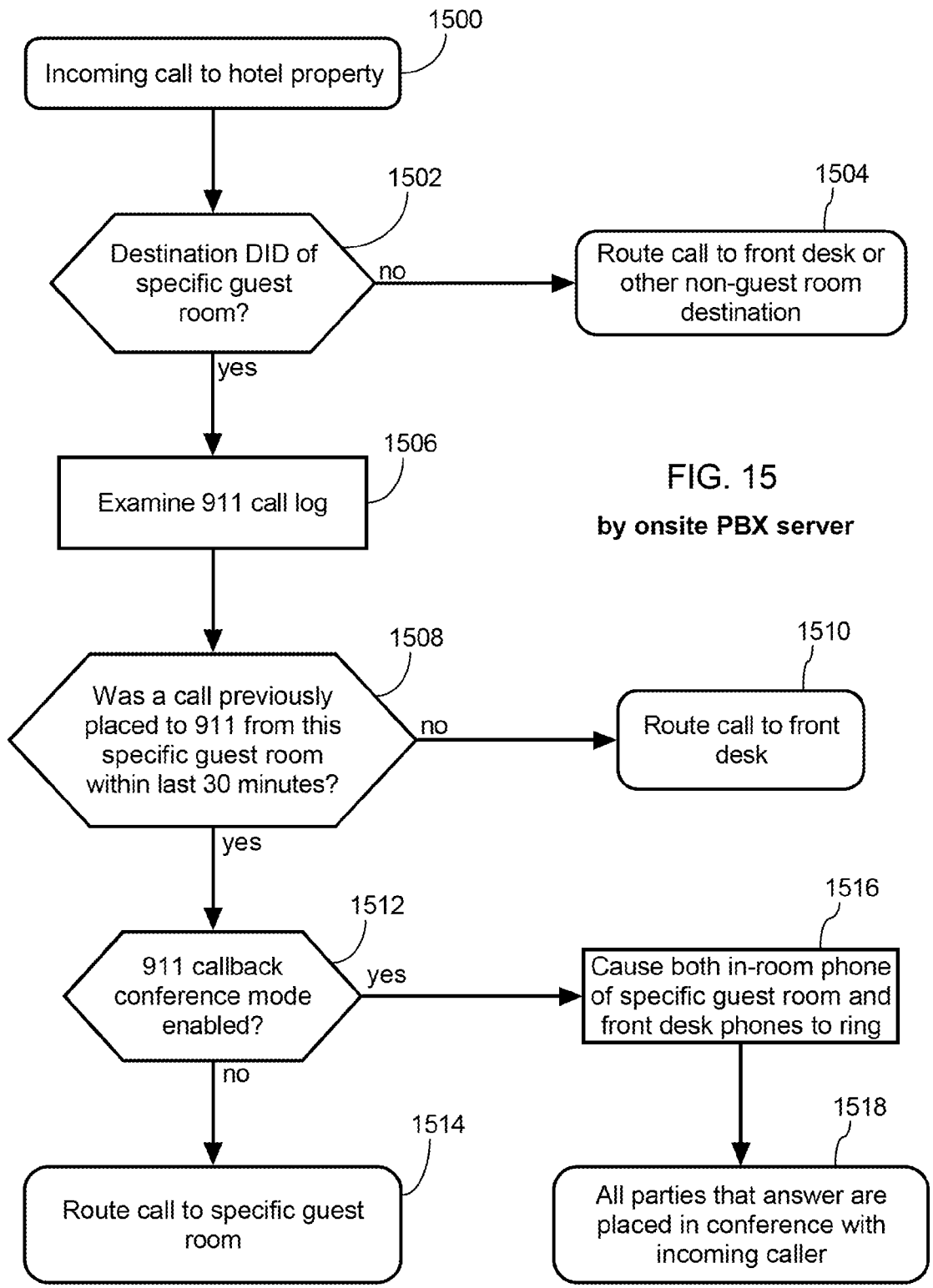

PROVIDING TO A PUBLIC-SAFETY ANSWERING POINT EMERGENCY INFORMATION ASSOCIATED WITH AN EMERGENCY CALL

CROSS-REFERENCE TO RELATED APPLICATIONS

This application is a Divisional application of U.S. patent application Ser. No. 14/557,369 filed Dec. 1, 2014, which claims the benefit of priority of U.S. Provisional Patent Application No. 61/910,858 filed Dec. 2, 2013 and U.S. Provisional Patent Application No. 61/952,088 filed Mar. 12, 2014; both of these applications are incorporated herein by reference.

BACKGROUND OF THE INVENTION (1) Field of the Invention

The invention pertains generally to enhancing information automatically made available at a public-safety answering point (PSAP) when an emergency call is placed. More specifically, the invention relates to automatically providing emergency information of the person experiencing the emergency to the PSAP operator who is handling the call.

(2) Description of the Related Art

When a guest staying in a hotel in North America needs emergency services such as police, fire, or ambulance, the guest will typically dial 9-1-1 using the telephone provided in their hotel room. The 9-1-1 call is recognized as an emergency call by the hotel's private branch exchange (PBX) and is connected to the local public-safety answer point (PSAP) that is responsible for serving the city or region at which the hotel is located.

Compliance with Enhanced 9-1-1 (E-911) requires automatically providing the PSAP operator with the physical location of the caller. For calls made from legacy hotels, the source caller ID (CID) associated with the emergency call will be the hotel's main phone number. In response to receiving the call, the PSAP computer system queries an automatic location information (ALI) database that maps the hotel's main phone number to the name and address of the hotel from which the call was placed. This information is displayed to the PSAP operator who can then dispatch emergency services to the hotel's location. However, since the specific location of the caller within the hotel is still unknown, the PSAP operator needs to verbally ask the caller for their specific room number.

In the event that that caller is unable to speak or the call is dropped before the PSAP operator obtains the room number, the PSAP operator must call the hotel's main number and ask the front desk staff which guest room is experiencing the emergency. The hotel's PBX system often includes an audit printer positioned near the front desk that automatically prints out a record of the guest room from which a call to 9-1-1 was placed along with the time and date of the call. By checking this printout front desk staff can help the PSAP operator direct emergency services to the correct guest room.

Delays in the PSAP operator obtaining the room number may significantly delay emergency service personal locating that person within the hotel. For this reason, in many states each hotel guest room is required by law to have a dedicated phone number (e.g., direct inward dial, DID). These dedicated phone numbers are each mapped to their respective room number of the hotel in the ALI database. As a result, when the PSAP receives an emergency call placed from a hotel guest room, the PSAP computer system queries the ALI database according to the source caller ID of the incoming call and obtains the name and address of the hotel along with the specific room number from which the call was placed. Beneficially, the PSAP operator is immediately aware of the exact room of the caller within the hotel and can dispatch emergency service providers to that location even if the caller is unable to speak.

A problem with current emergency dispatch systems is that the PSAP operators are only made aware of the location of the caller such as the name and address of the hotel and preferably also the room number within the hotel. However, often times there is additional information known in advance by the caller or the establishment from which the call was placed that would be useful for the PSAP operator. For example, many hospitality establishments such as hotels and long term care facilities are located near hospitals and guests staying at these establishments are undergoing or awaiting specific treatments. Further, some guests have known medical problems such as diabetes or allergies. It would be beneficial if the PSAP operator were automatically made aware of these and other kinds of personal emergency information upon receiving an emergency call rather than having to verbally obtain all such information from the caller or from a staff member at the establishment from which the call was placed.

BRIEF SUMMARY OF THE INVENTION

According to an exemplary embodiment of the invention, a system is disclosed that allows users to store personal emergency information. When the user thereafter places an emergency call, the user's saved personal emergency information is automatically made available to the public-safety answer point (PSAP).

In an exemplary embodiment of the invention, a user is enabled to enter personal emergency information when signing up for or modifying their account under a hotel chain's loyalty program. Thereafter, whenever the user is a guest staying at a hotel participating in the loyalty program, the user's loyalty program member number is correlated to the specific guest room that is assigned to the user. If an emergency call is placed from that guest room, the PSAP receives the call; queries an automatic location information (ALI) database in order to obtain the hotel name, address, and specific room number of the caller; and also queries an automatic emergency information (AEI) database to obtain the personal emergency information of the specific user who is currently checked-in to the hotel room from which the emergency call was placed. The PSAP operator is thereby automatically informed of both the specific location and the personal emergency information of the caller.

The AEI database may be pre-populated with records linking users to their currently assigned hotel rooms as guest's check-in and out of the hotel. The mapping may be done using the room numbers or the dedicated phone number for each room and may be updated as guests checked in at the hotel change over time. Alternatively, the mapping of a certain hotel room to a particular user identifier may be dynamically obtained in response to the query from the PSAP. For example, an AEI controller may query the property management system (PMS) at the hotel in order to obtain the loyalty program number of the guest currently checked into a room number specified by the PSAP, and then retrieve that guest's corresponding emergency information from the AEI database. In yet other embodiments, the hotel's PBX may provide the PSAP with the user identifier of the guest who is currently checked into the room from which the emergency call is placed. In this manner, the PSAP may directly query the AEI database to obtain the emergency information associated with the user identifier.

In another exemplary embodiment of the invention, a user is enabled to enter personal emergency information when signing up for or modifying their residential or mobile phone account. The user's emergency information is stored in an AEI database linked to their mobile phone number. Thereafter, if an emergency call is placed from that phone, the PSAP receives the call; determines the location of the caller by either querying the automatic location information (ALI) database or performing a wireless handset location determination process (e.g., radiolocation or GPS information received from handset); and then queries an automatic emergency information (AEI) database to obtain the personal emergency information of the caller.

In another exemplary embodiment of the invention, a user is enabled to enter personal emergency information when signing up for or modifying their residential or mobile phone account. The user's emergency information is stored in an AEI database linked to their mobile phone number. Thereafter, when an emergency call is placed from that phone, the PSAP receives the call and determines a type of the call according to information received along with the call. When the call is of a first type, the PSAP queries an automatic emergency information (AEI) database to obtain the personal emergency information of the caller. When the call is of a second type, the PSAP does not query the AEI database.

In another exemplary embodiment of the invention, a user is enabled to enter personal emergency information for storage in an automatic emergency information (AEI) database. The user's emergency information is stored in an AEI database linked to unique user identifier (UUID) for the user. Thereafter, if an emergency call is placed by the user, the phone or another device that handles the call is configured to include the user's UUID in the source caller ID information for the emergency call. The PSAP receives the call along with the UUID in the caller ID information; determines the location of the caller by either querying the automatic location information (ALI) database or performing a wireless handset location determination process (e.g., radiolocation or GPS information received from handset); and then queries the AEI database to obtain the personal emergency information associated with the user's UUID.

In an exemplary embodiment of the invention, a computer server or other device acting as a controller at a PSAP automatically receives personal emergency information associated with the caller placing the emergency call. The personal emergency information is communicated by the controller to a computer console corresponding to the operator handling the emergency call. A PSAP operator at the console can thereby rapidly dispatch appropriate emergency services according to the personal emergency information of the caller.

In an exemplary embodiment of the invention, surveillance is performed by remotely reconfiguring phones in the vicinity of a hotel guest room or other target location. Police may request that a target guest room be monitored and the onsite PBX server handling calls at the hotel determines which in-room phones are in the target guest room and then reconfigures those phones to open their microphones and/or turn on their video cameras. The reconfiguration may be done by the onsite PBX server creating a new configuration image with various settings such as auto answer: on, number of rings before answer: 1, ring volume: zero, speakerphone mode: on, video camera on by default: yes, etc. The onsite PBX server then reboots the phones at the target location so they will load the new configuration images. After an appropriate delay to allow the phones to boot up with the new settings, the onsite PBX server calls the phones and begins recording the audio/video data received from the phones. This configuration is in effect a new use for the auto-answer mode of phones to allow for remote police listening. The people in the room under surveillance may not be aware of the incoming call or that the police can now hear and or see everything within the vicinity of the phones in the room under surveillance. A similar process can also be utilized to monitor user's mobile phones by dynamically reconfiguring those phones in the same manner. For mobile phones, rather than the reconfiguration being done by the onsite PBX server at a hotel, the reconfiguration may be done the a server running on the user's mobile phone and/or telecom provider network.

In an exemplary embodiment of the invention, incoming calls are processed by an onsite or remote PBX server associated with a hotel in order to determine how to direct the incoming call at the hotel. When the destination number of the incoming call is a specific hotel room and the source caller ID of the phone call indicates that the call is being placed by a public-safety answering point (PSAP), the PBX server will route the incoming call so that it rings directly on the in-room phone in the specific guest room. This allows call back from PSAP to reach the caller in the fastest possible time. However, if the call is not answered within a predetermined time period such as the time required for three rings, the PBX server will either reroute or twin to the call to the front desk thereby allowing hotel staff to intervene and help the PSAP operator. On the other hand, if the destination number of the original incoming call is the specific hotel guest room but the source caller ID of the phone call does not indicate that it from the PSAP (i.e., the source phone number is not a predetermined number such as 9-1-1) then the PBX server instead first routes the call to the hotel front desk. This allows front desk to screen the call and thereby prevent telemarketers or other undesirable calls from being placed to guest rooms at the hotel.

In an exemplary embodiment of the invention, the hotel's PBX system follows standard NENA/PS ALI protocol and utilizes real DID numbers for each guest room. By following E-911, the PSAP operator is enabled to call the actual phone back that originated the PSAP call. However, to avoid misdials of the room's DID disturbing the guest in that room, not all incoming calls to the hotel PBX with a destination DID of the guest room will be routed directly to that guest room. When a particular guest room or DID number (e.g., "614-582-6514") calls 9-1-1, the PSAP sees all the PS/ALI data and if the line is disconnected can simply call the number back ringing the particular guest room or other telephone extension in the PBX associated with that DID number. However, in this embodiment, a timer variable allows for PSAP callback for only XX minutes, e.g., thirty minutes, after the call to 9-1-1 originated. In this way, the PSAP operator will be able to ring the in-room phone directly for thirty minutes after the call was originated. After that, the call is answered by the default answer point whether console or forward number.

In an exemplary embodiment of the invention, there is a programmable option or hardcoded setting for 9-1-1 callback conference so that when PSAP calls back the DID number from which an emergency call originated, they get placed in a conference call with both the extension related to that DID number and a secondary contact extension, for example, the front desk (programmable). In a use case scenario, when a guest dials 9-1-1 from their hotel room, the PSAP sees the DID of the in-room phone (e.g., '614-582-6514'). If the guest hangs up but the PSAP operator or other medical professionals need to ask questions, 9-1-1 calls back the DID (e.g., '614-582-6514'). The PBX server beneficially causes both the hotel front desk and the guest's in-room room phones ring because it determines that a 9-1-1 call was recently placed from this DID. All of the parties who answer at either or both of the front desk and the in-room phone are placed into conference. In the event the guest needs immediate medical assistance, front desk runs up to room and performs CPR or other first aid while EMS is on the way. After the 30 minutes (programmable) are expired since 9-1-1 was dialed, if an external caller dials the DID of the guest's room (e.g., "614-582-6514"), the PBX server routes the call only to the designated point (menu, voice prompt, front desk, voicemail, etc. because no call to 9-1-1 was recently (within 30 minutes) placed from the guest room associated with the DID. The default destination to which incoming calls outside the thirty minute window are routed may be programmable and avoids annoying the guest in that room with misdialed, non-emergency calls.

These and other advantages of the present invention will no doubt become apparent to those of ordinary skill in the art after reading the following detailed description of the preferred embodiment that is illustrated in the various figures and drawings.

BRIEF DESCRIPTION OF THE DRAWINGS

The invention will be described in greater detail with reference to the accompanying drawings which represent preferred embodiments thereof.

FIG. 2 is an example UI screen allowing a user to setup an advanced safety notification (ASN) feature and input personal emergency information for storage in a storage device such as the AEI database of FIG. 1.

FIG. 10 shows example caller ID values for emergency calls according to example embodiments of the invention.

FIG. 15 is a flowchart describing a method of handling incoming calls at a hospitality PBX according to another exemplary embodiment of the invention.

DETAILED DESCRIPTION

Figure 1:
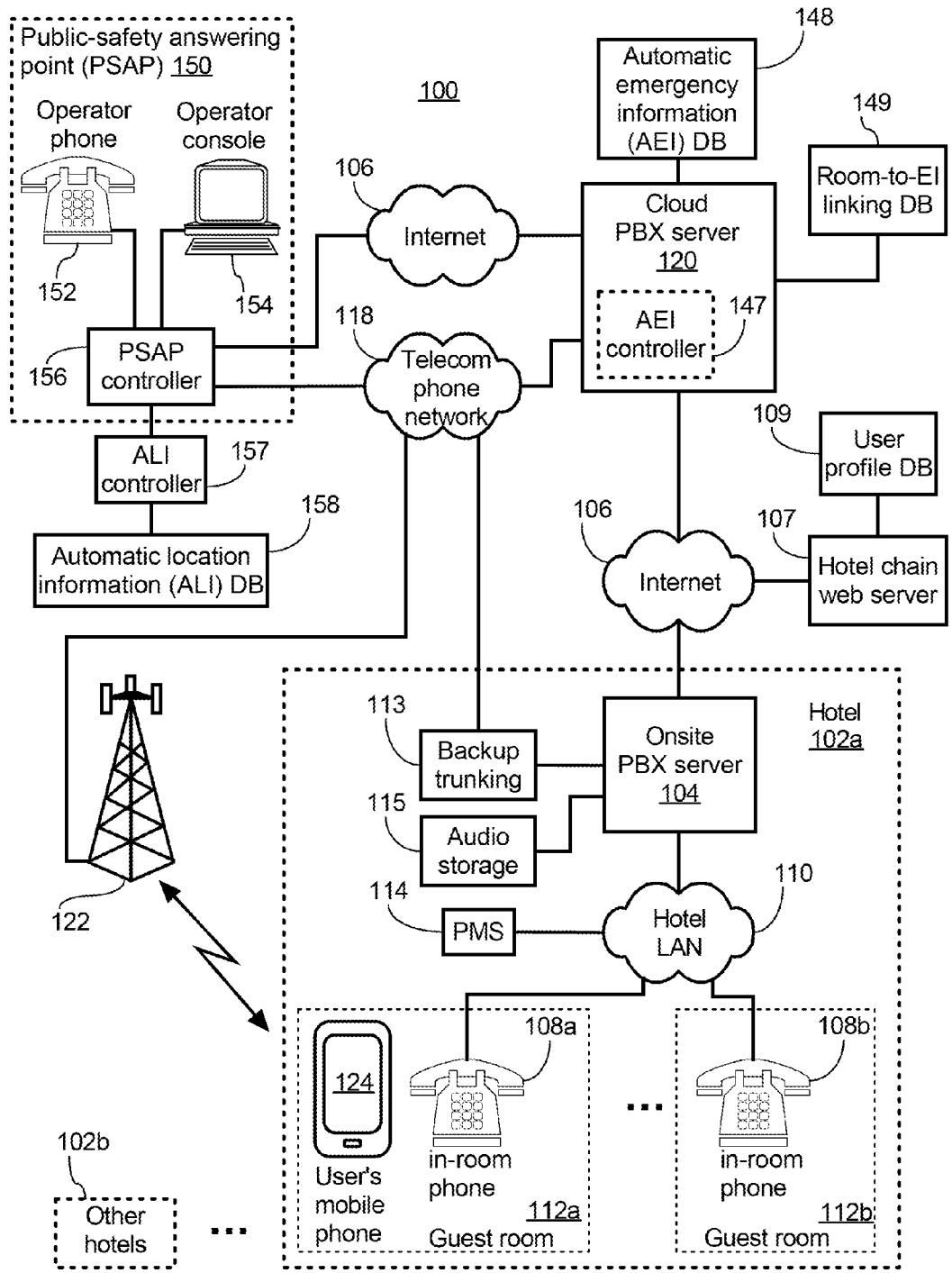
FIG. 1 shows a block diagram of a hybrid private branch exchange (PBX) system according to an exemplary embodiment of the invention.

FIG. 1 shows a hybrid private branch exchange (PBX) system 100 according to an exemplary embodiment of the invention. In this embodiment, the PBX system 100 provides telephone services at a plurality of hotels 102. As shown in FIG. 1, a first hotel 102*a* includes an onsite PBX server 104 coupled to the Internet 106. The onsite PBX server 104 is also coupled to a plurality of in-room phones 108 via the hotel's local area network (LAN) 110. In this example, each of the in-room phones 108 is located in a different guest room 112, namely, a first in-room phone 108*a* is located in a first guest room 112*a* and a second in-room phone 108*b* is located in a second guest room 112*b*. The hotel 102*a* also includes a property management system (PMS) 114, which manages guest check-ins and check-outs along with room assignments.

The onsite PBX server 104 handles all local telephone calls (i.e., peer-to-peer) between phones 108 at the hotel property. As such, the data representing local calls between in-room phones 108 does not need to be routed via the Internet 106. For calls that are incoming from or outgoing to external phone numbers via telecom phone network 118, the onsite PBX server 104 works in tandem with a cloud PBX server 120 so that data for external calls is routed through the Internet 106. For example, when a guest in a guest room 112 places an emergency (e.g., 9-1-1 call) using the in-room phone 108, the call is routed by the onsite PBX server 104 to the cloud PBX server 120, and then to the public-safety answer point (PSAP) 150.

The onsite PBX server 104 also includes audio storage 115, which may be stored on the storage media within the server 104 or another external component. The purpose of the audio storage is to record outgoing emergency calls placed from the hotel 102*a* for review by management and to record reverse 9-1-1 broadcast messages that are to be sent to the in-room phones 108 in the event of an emergency.

If either the cloud PBX server 120 or the hotel's 102*a* connection to the Internet 106 fails, backup trunking 113 is provided at the hotel 102 to connect to the telecom phone network 118 such as via plain old telephone service (POTS) lines.

The cloud PBX server 120 in this configuration acts as an automatic emergency information (AEI) controller 147 for accessing an AEI database 148. The AEI controller 147 and AEI database 148 work in tandem to provide to PSAP 150 personal emergency information associated with the guest of hotel room 112 from which an emergency call is placed.

Although only one hotel 102a is shown expanded in FIG. 1 so that the above described internal components are visible, the other hotels 102b may also include similar components.

The system 100 in this configuration further includes a hotel chain web server 107, which may be a part of the hotel's reservation system coupled to the Internet 106. The hotel chain web server 197 allows guests and travel agents to reserve hotel rooms at any of the hotels 102. Users may also input personal emergency information into the their accounts at the hotel chain web server 107 for storage in user profiles 109. Rather than or in addition to the cloud PBX server 120 acting AEI controller 147 to access the AEI database 148, the hotel chain web server 107 may act as an AEI controller for accessing personal emergency information stored in the user profile database 109. In other words, the hotel chain web server 107 may act as an AEI controller and the user profile database 109 may act as a AEI database in other embodiments. Other devices may likewise perform these function in other embodiments.

FIG. 1 illustrates a cell phone tower 122 coupled to the telecom phone network 118, and, in the following examples, cell phone tower 122 is assumed to provide adequate cell phone coverage to a user's mobile phone 124 shown located within the first guest room 108a. Mobile phone 124 in an example is a personal mobile phone brought to the hotel by the current user of the first guest room 112a, i.e., the currently registered guest of the first guest room 112a.

The system 100 of FIG. 1 also includes a public-safety answering point (PSAP) 150 housing at least one operator phone 152 and operator console 145 coupled to a PSAP controller 156. The PSAP 150 in this example is responsible for dispatching emergency services to the geographical area in which the hotel 102a is located. Whenever a guest or other user at the hotel 102a dials 9-1-1 from an in-room telephone 108, the call is routed by the onsite PBX server 104 and the cloud PBX server 120 to the PSAP controller 150, which passes it to an available operator phone 152.

To support Enhanced 9-1-1 (E-911) location detection, the PSAP controller 156 queries an automatic location information (ALI) controller 157/ALI database 158, which maps telephone numbers to physical addresses and may be managed by the local telecom provider. Further, the PSAP controller 156 in this embodiment also retrieves personal emergency information stored in the AEI database 148 from the AEI controller 147 (duties performed by the cloud PBX server 120 in this example). As a result, both the address information of hotel 102a and personal emergency information associated with the caller making the incoming emergency call are displayed to the PSAP operator by the operator's console 154. The operator may thereby dispatch emergency services such as an ambulance, fire, or police to the caller's location and can notify the emergency services of pertinent emergency information associated with the caller. Beneficially, the caller does not need to verbally relate to the operator all the pertinent emergency information thereby saving time. Also, if the caller is unable to speak, the PSAP operator is still aware of the caller's personal emergency information.

In this embodiment, both the onsite PBX server 104 and the cloud PBX server 120 are implemented as computer servers including well-known hardware such as processors, memory, and communications interfaces. For instance, the onsite PBX server 104 includes a one or more processors coupled to network interfaces and storage media. In this example, a first network interface is a cable modem coupled to the Internet 106, and a second network interface is an Ethernet interface coupled to hotel LAN 110, and the storage media is a combination of a hard drive and random access memory (RAM) storing data and software.

Similarly, the cloud PBX server 120 includes one or more processors coupled to network interfaces and storage media. In this example, the first network interface is internet protocol (IP) based interface providing connectivity to the telecom phone network (which may in fact be via the Internet 106), the second network interface is an Ethernet interface coupled to a gigabit Ethernet connection within an cloud hosting provider providing connectivity to the Internet 106, and the storage media is a combination of a hard drive and RAM storing, among other data and software, a room-to-emergency-information (EI) database 149.

Likewise, the other servers and controllers illustrated in FIG. 1 such as the PSAP controller 156, the ALI controller 157 and the hotel chain web server 107 may each respectively include one or more processors, network interfaces, and storage media in addition to other well-known hardware components typically included in a computer.

In the example embodiment of FIG. 1, the processors of the onsite PBX server 104, the cloud PBX server 120, the PSAP controller 156, the ALI controller 157, and the hotel chain web server 107 execute various computer programs (i.e., computer executable instructions) loaded from non-transitory storage media such as random accessible memory (RAM) devices, FLASH or other non-volatile memory devices, and/or hard disk drives. The processors are configured via the computer programs to perform various functions as described in the following. In the following description, the plural form of the word "processors" is utilized as it is common for a central processing unit (CPU) of a computer server to have multiple processors (sometimes also referred to as cores); however, it is to be understood that a single processor may also be configured to perform the below-described functionality in other implementations.

FIG. 2 is an example UI screen 200 allowing a user to setup an advanced safety notification (ASN) feature and input personal emergency information for storage in a storage device such as the AEI database 148. The ASN feature enables a guest to customize his or her medical and other personal emergency information via a link on the hotel's respective brand web page. The ASN information setup by the user is fed to the AEI database 148 cloud database. While the guest is checked in to the hotel, the ASN feature causes the user's personal emergency info inputted at this screen to be sent to the PSAP 150. In this example, the UI screen 200 is a web page displayed on the user's mobile phone 124 or another web-capable device operated by the user such as a laptop or tablet computer. The UI screen 200 may be provided by the hotel chain web server 107 such as when the user makes a reservation at the hotel or modifies their loyalty program member details.

A first section 202 of the UI screen 200 displays to the user their loyalty program membership number along with their name as specified on the account. An "edit" button 204 allows the user to update their name such as to correct spelling errors or if a name change occurs. In some embodiments, the membership number is predetermined (generated and stored) by the hotel chain web server 107; however, it is to be understood that in other embodiments the membership number may be any unique identifier for the user and may be entered by the user rather than automatically generated by the hotel chain web server 107.

A second section 206 is a text box allowing the user to enter any personal emergency information that they feel may be relevant in the event of an emergency involving the user.

As shown in the example of FIG. 2, the user has entered their known medical conditions that would relevant and important to emergency service providers (e.g., first responders such as ambulance, fire and/or police). Additionally, the user has included in the personal emergency information section 206 the contact details of both the user's family and the user's doctor. Other users may choose to enter different personal emergency information in this box 206 such as the user's medical alert number. It is up to the user to decide what information, if any, to include. Each user's information is securely stored within their own user profile in the user profile database 109 and is not accessible to other users.

In an embodiment of the invention, staff at the hotel are also blocked from accessing any user's personal emergency information entered at UI screen 200 unless an emergency call is placed from a guest's registered guest room 108. After the onsite PBX server 104 detects that an emergency call has been placed from a particular guest room 112a, a computer terminal accessible to hotel staff at the front desk allows access to the personal emergency information for the user currently checked in to the particular guest room 112a. In this way, should the PSAP operator have to call the hotel front desk to coordinate or discuss the call, both the PSAP operator and the hotel front desk staff are aware of the guest's personal emergency information.

A third section 208 enables the user to activate automatically providing the personal emergency information to the public-safety answer point (PSAP) if an emergency call is placed from the guest's hotel room. One benefit of having this functionality be a user-configurable setting is to enable the user to shut it off in the event they are not the actual user staying in the guest room. This situation may occur when a user books a hotel room for someone else, for example.

When the user selects "Yes" for setting 208 as shown in FIG. 2, the user's personal emergency information is automatically stored in the AEI database 148. In this embodiment, the hotel chain web server 107 communicates the user's personal emergency information entered at UI screen 200 from the user profile database 109 to the AEI database 148 at the time the user presses the save button 210. However, in other embodiments the user's emergency info may be stored in the AEI database 148 at other times such in response to the user checking in to a hotel 102a, when an emergency call is paced from the user's assigned room at the hotel 102, and/or in response to the AEI controller 147 receiving a query from the PSAP controller 156 after an emergency call has been made by the user.

Figure 3:
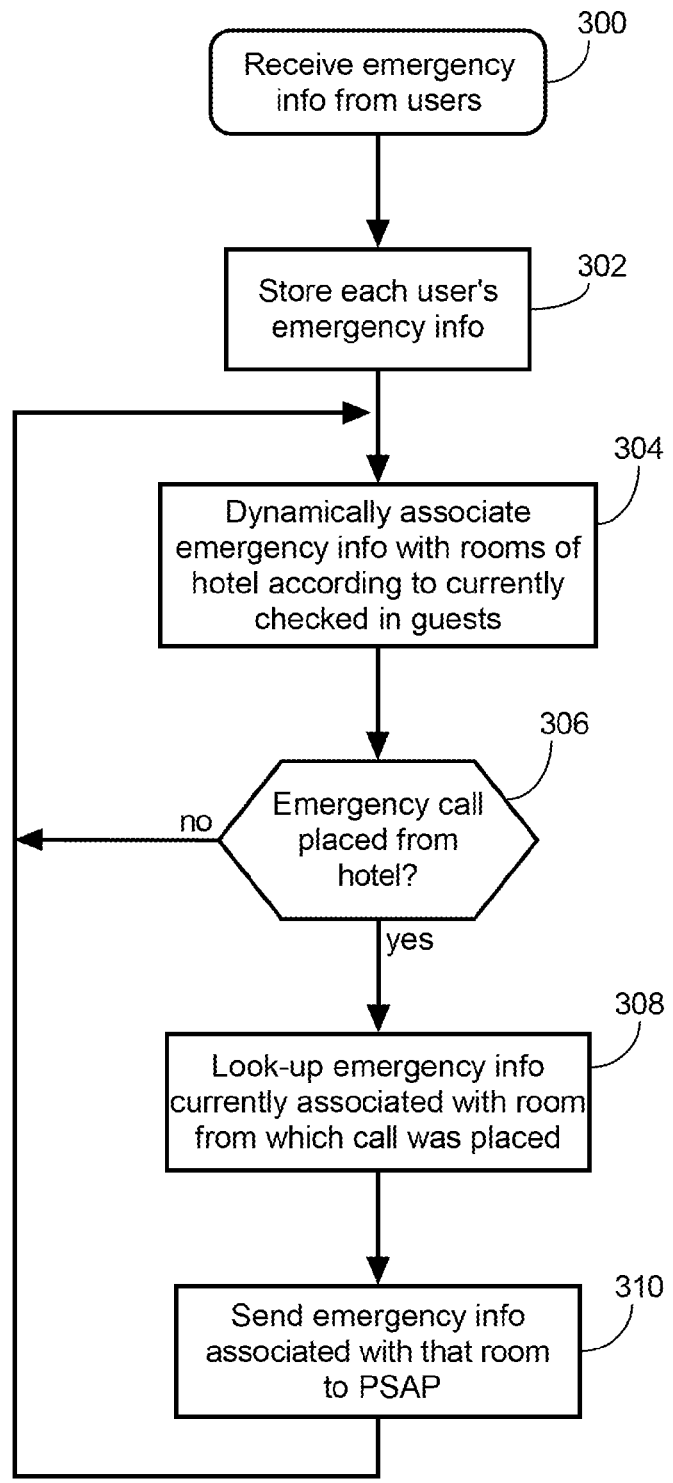
FIG. 3 is a flowchart describing a method of providing the PSAP with personal emergency information associated with an incoming emergency call according to an exemplary embodiment of the invention.

FIG. 3 is a flowchart describing a method of providing the PSAP 150 with personal emergency information associated with an incoming emergency call according to an exemplary embodiment of the invention. With reference to FIG. 1, the steps of FIG. 3 may be performed by the processors of the onsite PBX server 104, the cloud PBX server 120, the hotel chain web server 107, and/or the PSAP controller 156 as indicated below. Alternatively, the steps may be performed by another device different than the device specified below. The steps of the flowchart are not restricted to the exact order shown, and, in other configurations, shown steps may be omitted or other intermediate steps added. In this embodiment, the system 100 operates as follows:

Step 300 involves receiving personal emergency information from users. In an example, the hotel chain web server 107 receives emergency information from a plurality of different users as each user signs up for the hotel chain's loyalty program. As a part of the sign-up process and at any time thereafter, each user fills out the configuration fields 202, 206, 208, 209 shown in the UI screen 200 of FIG. 2. Different users have different user identifiers; for example, each user is assigned a unique user identifier as a part of the sign-up process, and the user identifier for a particular user may be that particular user's membership number (displayed on the first row of section 202 of FIG. 2).

Step 302 involves storing each user's emergency information along with the user's associated user identifier in a storage device. Continuing the above example, the web server 107 saves each user's personal emergency information in both the user profile database 109 and the AEI database 148. The user's other loyalty program information such as smoking/non-smoking room preferences are only stored in the user profile database 109 and are not stored in the AEI database 148 in this configuration. However, as mentioned above, the AEI database 148 and the user profile database 109 may in fact be the same database stored in a same storage device in some embodiments. Alternatively, the AEI controller 147 may have a database communication link to the user profile database 109 in order to retrieve personal emergency information stored therein. The saving step for a particular user may occur when the particular user clicks the "Save changes" button 210 in FIG. 2.

Step 304 involves dynamically associating emergency info with rooms of the hotel according to currently check in guests at the hotel. For example, when a guest makes a reservation, the guest provides their loyalty program membership number as a part of their reservation details. Then, at check-in the hotel's PMS 114 associates the guest's loyalty number and other details of the guest with the guest's currently assigned room 112 at the hotel 102. The onsite PBX server 104 receives the check-in message from the PMS 114 and passes the user identifier and room details to the AEI controller 147 for storage in the AEI database 148. At check-out the PMS 114 un-associates the guest's loyalty number with the guest room 112, and the onsite PBX server 104 informs the AEI controller 147 of the user's check-out so that the AEI controller 147 can un-associate the user's personal emergency information with the now vacant room 112 in the AEI database 148. The process repeats for each new guest that checks in to the hotel 102.

In the event a checked-in guest does not have a loyalty program number, the PMS 114 will specify a "0" or another predetermined value in the user identifier field of the room details representing that a guest is checked in to the room 112 without a loyalty program membership number. A different predetermined value such as a NULL may be specified in the user identifier field of the room details to represent that a room 112 is vacant. In this embodiment, each user's personal emergency information is pre-stored in the AEI database 148 and is associated with the user's loyalty program membership number. This happens automatically when the user presses the save button 210 in FIG. 2. Further, in response to check-in and check-out messages received from the PMS 114, the AEI controller 147 dynamically associates and un-associates users' personal emergency information with specific rooms 112 of the hotels 102.

For example, step 304 may involve the AEI controller 147 temporarily mapping a user identifier with either the room number or the phone number of a particular guest room 112 at the hotel 102. When a guest checks in to a particular guest room 112 at the hotel 102, the PMS 114 sends a check-in message to the onsite PBX server 104 via hotel LAN 110, and the onsite PBX server 104 forwards this message up to the cloud PBX server 120 via the Internet 106. The AEI controller 147 running on the cloud PBX server 120 receives the check-in message and saves a temporary correlation between the room number or the phone number of the particular guest room 112 with the user identifier the of the guest now checked in to the particular guest room 112. Because the user's emergency information is also stored in the AEI database 148 associated with the user's identifier, the AEI controller 147 has in effect associated the user's room 112a (either referenced by phone # or room #) with the user's personal emergency information via the user's identifier.

In another example, either the onsite PBX server 104, the cloud PBX server 120 and/or the AEI controller 147 may periodically or otherwise poll the PMS 114 at the hotel to retrieve current information of the hotel rooms 112. This current information will specify the user identifier associated with each currently checked in guests along with their assigned room numbers. In this way, the AEI database 148 is dynamically updated by the AEI controller 147 to link specific user identifiers (and thereby their associated personal emergency information) with specific rooms 112 of the hotels 102.

Step 306 involves determining whether an emergency call has been placed from the hotel 102a. In an example, the PSAP controller 156 checks whether an emergency call originated from the hotel 102a by performing an automated location determination on each incoming emergency call. In particular, the PSAP controller 156 queries the ALI controller 157/ALI database 158 according to the source caller ID of each incoming emergency call. When the PSAP controller 156 finds that an incoming emergency call originated from a guest room of the hotel 102a (i.e., because the ALI database indicates the hotel address and room number), the process of FIG. 3 proceeds to step 308; otherwise, the process returns to step 306 to check whether a subsequent incoming emergency call at the PSAP 150 originated from the hotel 102a.

In another example of step 306, the onsite PBX server 104 and/or the cloud PBX server 120 determine whether an emergency call has been placed from the hotel 102a by checking all outgoing calls. Each outgoing call made from an in-room phones 108 is processed by the onsite/cloud PBX servers 104, 120 to check whether the destination phone number is 9-1-1 (or another predetermined emergency telephone number). In this example, when either the onsite/cloud PBX server 104, 120 determines that an outgoing call from the hotel 102 is an emergency call, the process of FIG. 3 proceeds to step 308; otherwise, the process returns to step 306 to check whether a subsequent outgoing call from the hotel 102 is an emergency call.

Step 308 involves looking up the personal emergency information that is currently associated with the hotel guest room 112 from which the emergency call was placed. Once the guest room from which the emergency call was placed is determined, the personal emergency information associated with that room 112 is obtained as a result of the dynamic associations performed at step 304.

For example, assume at step 304 that the PMS 114 information reported to the AEI controller 147 specifies the unique user identifier and assigned room number for all currently checked in guests at the hotel 102. Step 308 then involves the AEI controller 147 firstly looking up in the AEI database 148 the user identifier associated with the specific room 112 from which the emergency call was placed, and secondly looking up in the AEI database 148 the personal emergency information that is associated with that user identifier.

In another example, assume step 304 involves the AEI controller 147 updating the records in the AEI database 148 to store which emergency information is associated with which room number as the guests check in and out at the hotel. Step 308 then involves the AEI controller 147 looking up the emergency information in the AEI database 148 that is currently associated with the room from which the emergency call was placed.

Concerning how the AEI controller 147 knows the room from which the emergency call was placed, this could by the onsite/cloud PBX server(s) 104, 120 looking at the source caller ID of an outgoing emergency call placed from the hotel 102 and mapping that to a particular guest room 112 from which the call was placed. Alternatively, the AEI controller 147 may instead receive a query from the PSAP controller 156 and the query specifies either 1) a particular phone number uniquely associated with the guest room from which the emergency call was placed, 2) the room number itself, or 3) any other identifier of the guest room or the user from which the call was placed.

Step 310 involves the AEI controller 147 sending the personal emergency information associated with the hotel guest room 112 from which the emergency call was placed to the PSAP controller 156 assuming the user has selected "yes" at field 208 of FIG. 2, which enables this functionality. In an embodiment, step 310 is omitted and user's personal emergency information is not sent to the PSAP whenever the user has selected "no" at field 208 of the user's ASN setup shown in FIG. 2.

Assuming the user has selected "yes" at field 208, step 310 is performed by the AEI controller 147 in response to receiving a query from the PSAP controller 156 requesting the emergency info associated with a specific phone number corresponding to a room 112 or a specific room number at the hotel 102a. For example, the PSAP controller 156 is running an application that causes the PSAP controller 156 to query the AEI controller 147 with an HTTP request, and the personal emergency information is sent by the AEI controller 147 to the PSAP controller 156 via an HTTP response. Of course, other networking protocols other than HTTP may be utilized in other embodiments to for the PSAP controller 156 to request and receive the personal emergency information for a particular guest room at the hotel. For example, the PSAP controller 156 may have a database link to the AEI database 148 via the Internet 106, the telecom phone network 118, or another communications link. In another embodiment, the AEI database 148 and the ALE database 158 may be the same database storing both location information and personal emergency information associated with phone numbers.

In another example embodiment, the sending action of step 310 is performed by the AEI controller 147 is response to detecting that an emergency call has been placed from a particular guest room 112 of the hotel without needing to receive a query from PSAP controller 156. In this embodiment, the personal emergency information can be sent by the AEI controller 147 to the PSAP controller 156 via an e-mail message, a text message (e.g., short message service, SMS), a media message (e.g., multimedia messaging service, MMS), or a predetermined API with the PSAP controller 156 in order to push the personal emergency information to the PSAP 150.

After the emergency information is sent to the PSAP at step 310, the PSAP controller 156 displays it on the 9-1-1 operator screen 154. The PSAP controller 156 may further send it to one or more emergency medical service (EMS) responding vehicles that is/are on route to the scene, or via SMS, MMS, e-mail, or other protocol to the first responder's mobile phone. Sending to each of the EMS vehicles and first responders may be under the control of the PSAP operator.

Alternatively, the PSAP controller 156 may be configured in an exemplary embodiment to automatically send the personal emergency information received at step 310 to all of the responding EMS vehicles and personnel as soon as they are assigned to respond to the call by the PSAP operator.

In an exemplary embodiment of the invention, first responders are better able to meet the needs of the caller experiencing the emergency. For example, prior knowledge of the personal emergency information of the caller may allow the first responders to prepare and dispatch required medical equipment before leaving base and to be better prepared to handle any special needs of the caller immediately upon arrival. Hotels near hospitals that typically house patients waiting for or recovering from surgery, nursing and acute care facilities, and hotels and resorts in senior citizen resort areas where instances of medical attention are higher are also better able to assist any guests who call 9-1-1.

Figure 4:
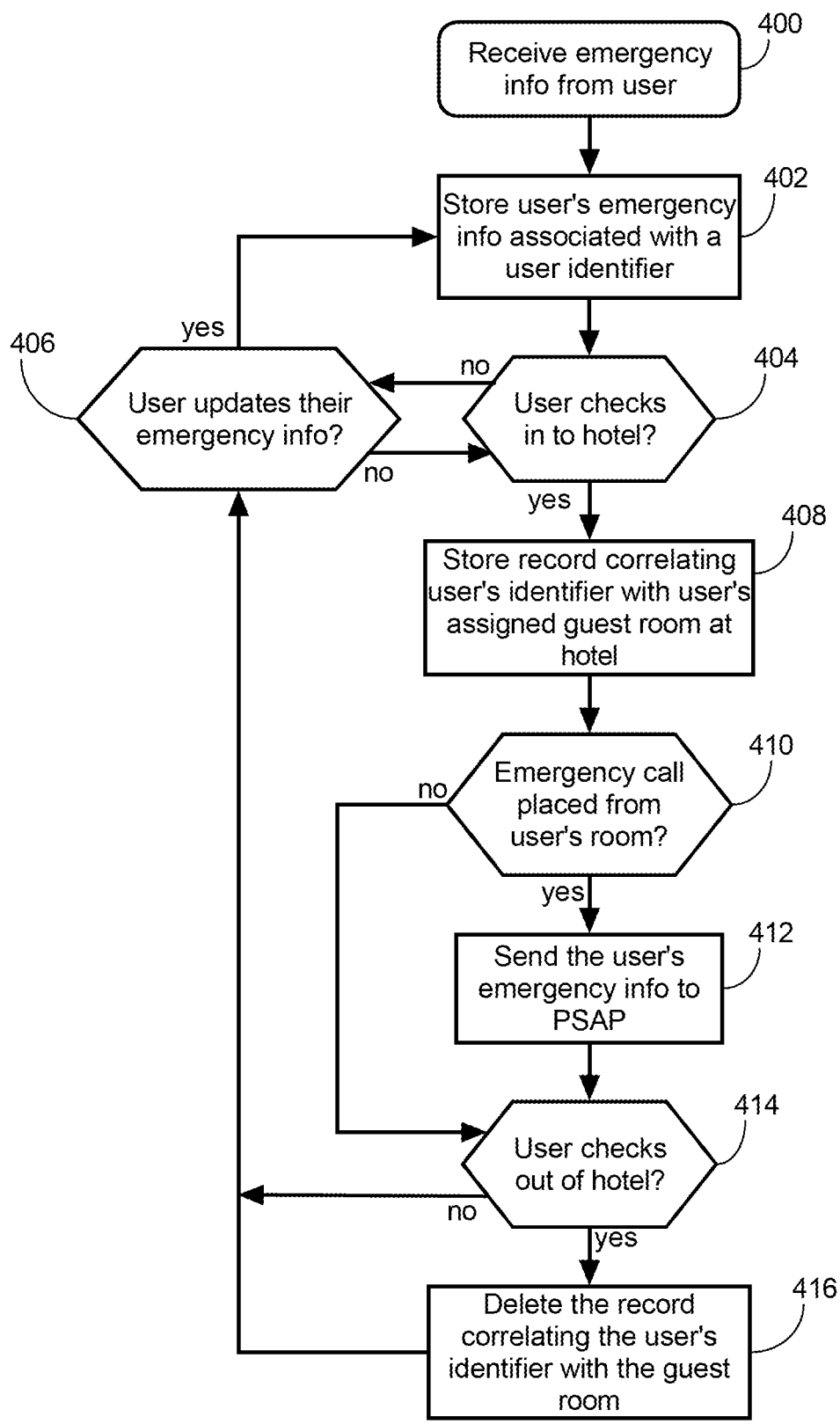
FIG. 4 is a flowchart describing a method of providing personalized emergency information for emergency calls according to an exemplary embodiment of the invention.

FIG. 4 is a flowchart describing a method of providing personalized emergency information for emergency calls according to an exemplary embodiment of the invention. With reference to FIG. 1, the steps of FIG. 4 may be performed by the processors of the onsite PBX server 104 and the cloud PBX server 120 as indicated below. Alternatively, the steps may be performed by another device different than the device specified below. The steps of the flowchart are not restricted to the exact order shown, and, in other configurations, shown steps may be omitted or other intermediate steps added. In this embodiment, the system 100 operates as follows:

At step 400, a user's personal emergency information is received via UI screen 200 shown in FIG. 2. However, rather than the UI screen 200 being provided by the hotel chain web server 107, in this embodiment, the cloud PBX server 120 also includes web server functionality and users are able to setup a personal account with the cloud PBX provider. The purpose is to allow the AEI controller 147 in the cloud PBX server 120 to provide the user's personal emergency information to the PSAP 150 while the guest is checked in to any of the hotels 102 that contract with the cloud PBX provider. In this embodiment, the user may enter multiple hotel loyalty numbers in field 204 of UI screen 200 by pressing the "Add" button 205. This is beneficial so that the user can benefit from the below functionality regardless of the different brands of hotels.

At step 402, after the user has entered their various loyalty program numbers in field 202 and personal emergency information in field 206, the user presses the "Save changes" button 210 and the entered information is then stored by the AEI controller 147 in the AEI database 148. The saved personal emergency information is thereby associated with all of the user's different loyalty program numbers across different hotel brands in the AEI database 148. In this way, each user does not need to enter their personal emergency information in each of the different brand's own loyalty program user profiles 109 but can enter it once with the cloud PBX provider for storage in the central AEI database 148.

At step 404, the onsite PBX server 104 detects whether the user has checked in to any of the hotels 102. Similar to as described above, the onsite PBX server 104 at each hotel 102 may receive check-in messages from the PMS 114 at the same hotel 102. Rather than receiving these messages from the PMS 114 in an interrupt fashion, the onsite PBX server 104 may also poll the PMS 114 for its stored room details and compare the received room details with a stored copy of the previous room details in order to detect differences (i.e., check-ins and/or check-outs). When a check-in for the user has occurred the onsite PBX server 104 sends a check-in message for the user along with their loyalty program membership number, hotel information, and assigned room information to the cloud PBX server 120 and control proceeds to step 408; otherwise, control proceeds to step 406 to check whether the user's has updated their emergency info.

At step 406, the cloud PBX server 120 determines whether the user has updated their personal emergency information settings in UI screen 200. In this embodiment, the user may at any time log back into their account at the cloud PBX server 120 via any internet-connected device (e.g., the user's mobile phone 124 or another web-enabled computer) and make changes such as adding new pertinent emergency information in box 206. For example, the user may wish to change their emergency contact information depending on who they are travelling with or add a medical condition after receiving a diagnoses. Alternatively, the user may wish to edit 204 or add 205 membership information such as the user's unique identifier at other hotels 102b. If the user has made a change to their information, control returns to step 402 to save the updated info into the AEI database 148. Otherwise, the control returns to step 404 to check if the user has now checked in to a hotel 102.

At step 408, because the cloud PBX server 120 has now received a check-in message indicating that the user has checked in to a particular room 112 of a particular hotel 102, the AEI controller 147 stores a record in the AEI database 148 to correlate the user's identifier with the user's assigned guest room 112 at the hotel 102. For example, if the check-in message indicates that a guest using user identifier "234-135-876" has checked into room 112a at hotel 102a, then the AEI controller 147 stores a mapping from the hotel 102a and room 112a combination to the user's identifier (e.g., a mapping of "Hotel 102a; Room 112a"->"234-135-876") in the AEI database 148. In this example, the reference numerals illustrated in FIG. 1 are utilized as the hotel and room identifiers for convenience of illustration, but of course other identifiers could also be utilized.

In another embodiment where each hotel room 112 has a unique telephone number (e.g., its own DID), the AEI controller 147 stores a mapping from the unique phone number of the user's room to the user's identifier (e.g., a mapping of "$Phone_number_for_room_112a_of_hotel_102a"->"234-135-876").

At step 410, the onsite and/or cloud PBX server(s) 104, 120 detect whether an emergency call has been placed from the user's guest room 112a. For instance, by checking whether the destination phone number of an outgoing call from the user's room 112a is 9-1-1, the servers 104, 120 can determine if the call is an emergency call. When yes, control proceeds to step 412; otherwise, if no call is made or if an ordinary (i.e., a non-emergency) call is placed, normal call handling is performed and control proceeds to step 414.

At step 412, because the outgoing call is an emergency call, the AEI controller 147 running on the cloud PBX server 120 looks up the user's personal emergency information in the AEI database 148 according to, for example, the source room from which the call was placed, the source telephone number from which the call was placed, or the user identifier of the user that is currently checked in to the room from which the call was placed and then sends the associated personal emergency information to the PSAP 150.

The user's emergency information in this embodiment is pushed to the PSAP 150 along with the emergency call without waiting for a query from the PSAP 150. In an example, the user's personal emergency is e-mailed or otherwise messaged to the PSAP controller 156. The message sent from the AEI controller 147 to the PSAP controller 156 includes details of the emergency call to allow the PSAP operator to quickly identify to which call it pertains. For example, the subject of the e-mail or other message may identify the source caller ID of the emergency call to allow for easy correlation to that call by the PSAP controller 156. Other details of the emergency call are also included including the time and date of the call, the hotel name and room number, in addition to the personal emergency information of the user checked in to the room at the time the call is placed.

In another embodiment, step 412 involves the AEI controller 147 receiving a query from the PSAP controller 156 requesting the personal emergency information associated with a particular hotel 102*a* and room number 112*a*, or another target query. The AEI controller 147 looks up the requested personal emergency information and sends it to the PSAP controller 156 in response to the query. Further explanation of this embodiment is provided later in this disclosure with reference to FIG. 5.

At step 414, the onsite PBX server 104 detects whether the user has now checked out of their assigned hotel room 112*a*. The onsite PBX server 104 at the hotel 102*a* may receive check-out messages from the PMS 114 at the hotel 102*a*, or, rather than receiving these messages from the PMS 114 in an interrupt fashion, the onsite PBX server 104 may also poll the PMS 114 for its stored room details and compare the received room details with a stored copy of the previous room details in order to detect differences (i.e., check-ins and/or check-outs). When a check-out for the user has occurred, the onsite PBX server 104 sends a check-out message for the user to the cloud PBX server 120 and control proceeds to step 416; otherwise, control returns to step 406 to determine whether the user has updated their emergency info.

At step 416, because the user has now checked out of the room, the cloud PBX server 120 acting as the AEI controller 147 deletes the record correlating the guest room number (or the phone number of the guest room) with the user's identifier in the AEI database 148.

After deleting the record for the particular guest room number or guest room phone number, if a subsequent emergency call is placed from that guest room, there will be no user identifier associated with the room. Therefore, the AEI controller 147 will not send any user's personal emergency information to the PSAP controller 156. This may be the case, for example, if a maid calls 9-1-1 from the guest room while the room is vacant. Since the room is not currently assigned to any guest, the call will still go through to the PSAP 150 but there is no personal emergency information to send to the PSAP 150. Similarly, after a next guest checks in to the room, the processes for that guest will proceed from step 404 of FIG. 4 and that guest's personal emergency information will be sent by the AEI controller 147 at step 306 to the PSAP controller 156 in the event that an emergency call is placed from the room. Thus, in this embodiment, the system will only send the emergency information corresponding to the currently registered guest of room 112*a* when an emergency call is placed from that room 112*a*.

Figure 5:
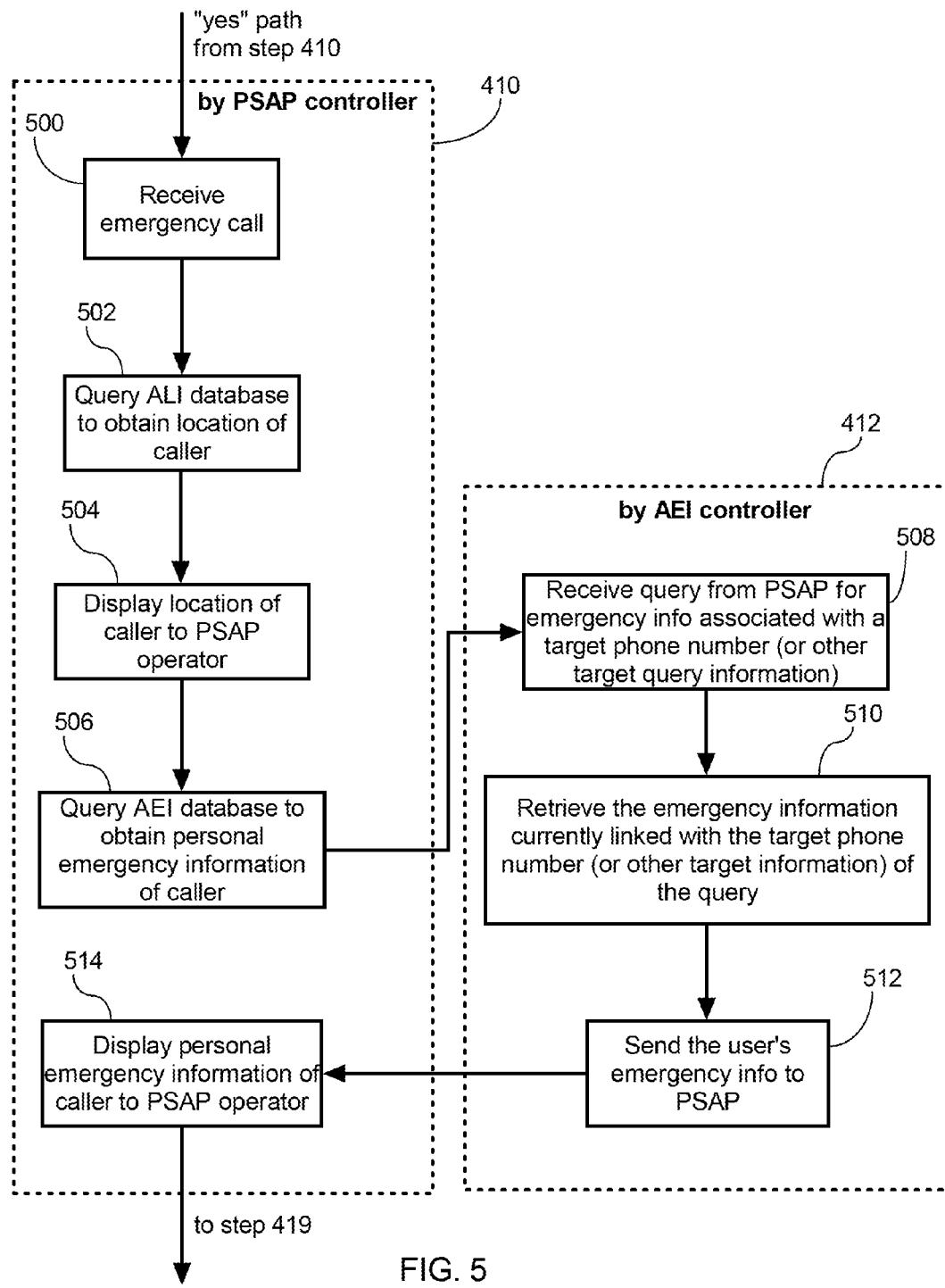
FIG. 5 illustrates a flowchart describing a method of providing personalized emergency information for emergency calls according to an exemplary embodiment of the invention.

FIG. 5 illustrates a flowchart describing a method of providing personalized emergency information for emergency calls according to an exemplary embodiment of the invention. In this embodiment, steps 410 and 412 of FIG. 4 explained above are replaced with the combined steps performed by the PSAP controller 156 and AEI controller 147 as shown in FIG. 5. Alternatively, the steps may be performed by another device different than the device specified below. The steps of the flowchart are not restricted to the exact order shown, and, in other configurations, shown steps may be omitted or other intermediate steps added. In this embodiment, the system 100 operates as follows:

At step 500, the PSAP controller 156 receives an incoming emergency call. The emergency call has a source caller ID phone number, for example, the dedicated phone number of a particular guest room 112*a* of the hotel 102*a*. A caller ID name field including other details of the incoming call may also be populated with other information.

At step 502, the PSAP controller 156 queries the ALI controller 157/ALI database 158 in order to lookup the physical location that is associated with the source caller ID of the incoming emergency call. In response, the ALI controller 157 replies with the name and address of the hotel 102 along with the room number 112*a* within the hotel 102 that are mapped to the source caller ID in the ALI database 158.

Other methods of determining the location of the caller may also be performed at step 502 as required. For example, if an emergency call is placed from a mobile (e.g., wireless) phone 124, its location may be determined via cell tower 122 triangulation or GPS to specific coordinates and further mapped to a particular range of geographical location(s) such as street addresses or building/room names and numbers. These other location detection methods are known in the art and further explanation is omitted herein.

At step 504, the PSAP controller 156 sends the caller location information to the operator console 154 for display. In this manner, the PSAP operator can answer the incoming emergency call using operator phone 152 and see the location information of the caller on operator console 154.

At step 506, the PSAP controller 156 queries the AEI controller 147/AEI database 148 in order to look-up and retrieve the personal emergency information that is associated with target query information. In this embodiment, the target query information is determined according to the source caller ID details of the incoming emergency call. For instance, the PSAP controller 156 extracts certain information from the caller ID fields of the incoming emergency call and then queries the AEI controller 156 to find out whether there is any personal emergency information associated with that target query information.

In an example, the PSAP controller 156 performs step 506 by querying for the source caller ID phone number of the incoming call. This action may be done by the PSAP controller 156 for every incoming emergency call so that emergency information associated with each call's different source phone number is found. In this way, in addition to personal emergency information of a currently checked in guest at a hotel 102, an individual user may also store in the AEI database 148 personal emergency information associated with the phone number of their personal mobile phone 124.

In other embodiments, the PSAP controller 156 may only query the AEI controller 147 when the source caller ID phone number and/or name, and/or the address information of the caller match a predetermined list. The predetermined list may include the names/addresses of hotels and other establishments that store personal emergency information in the AEI database 148.

In yet other embodiments, the source caller ID name and phone number fields may include a tag or other identifier that indicates to the PSAP controller 156 that personal emergency information is or may be available in the AEI database 148. When the PSAP controller 156 sees the tag or other identifier, the PSAP controller 156 will perform the query at step 506 using the tag, other identifier, or the other information included in the caller ID field as the target query information. In one configuration, the PSAP controller 156 queries the AEI database 148 at step 506 if and only if the source caller ID information of the incoming emergency call includes a recognized tag or other identifier indicating personal emergency information may be available within AEI database 148.

At step 508, the AEI controller 147 receives the query from the PSAP controller 156. In some embodiments the query may be an HTTP request made by the PSAP controller 156 to a predetermined URL served by the AEI controller 147.

The request received by the AEI controller 147 at this step includes the target query information determined by the PSAP controller 156 at step 506. As above, examples of the target query information include, but are not limited to, one or more of: the source caller ID phone number of the emergency call received at the PSAP controller 156, the source caller ID name of the emergency call received at the PSAP controller 156, an identifier or other tag included in or associated with information in either the caller ID phone number or name fields of the emergency call received at the PSAP controller 156; and/or an identification of the hotel name, address, GPS coordinates, cell tower 122 proximity, specific guest room, and/or any other information regarding the location from which the emergency call was placed. For example, according to location information retrieved by the PSAP controller 156 from the ALI database 158 at step 502.

At step 510, the AEI controller 147 retrieves from the AEI database 148 the personal emergency information that is associated with the target query information. For example, assuming the target query information queried by the PSAP controller 156 is the source caller ID phone number, the AEI controller 147 at this step looks up in the AEI database 148 to find the user identifier that is currently mapped to the phone number. As described above for step 408, this mapping was previously stored in the AEI database 148 when the user checked into their assigned hotel room.

Alternatively, the AEI controller 147 may perform multiple queries on the AEI database 148 to determine the user identifier currently associated with the source caller ID phone number queried by the PSAP controller 156. For example, the AEI controller 147 may first find the specific hotel 102 and guest room 112 that are mapped to the source caller ID phone number, then find the user identifier for the guest who is currently checked in to that guest room 112.

Once the AEI controller 147 has found the user identifier associated with the target query information, the AEI controller 147 retrieves the personal emergency information associated with that user identifier from the AEI database 148. For example, assuming the target query information queried by the PSAP controller 156 is found to be associated with user identifier "234-135-876", the AEI controller 147 will retrieve the personal emergency information (e.g., as entered by the user in field 206 of FIG. 2) for that user identifier from the AEI database 148.

Although in the above examples the AEI controller 147 links the target query information to the emergency information by first finding the user's identifier associated with the target query and then finding the emergency info associated with the user identifier, the process used by the AEI controller 147 at step 510 depends on the data organization of the AEI database 147. In general there will be some chain of associations linking the target query information to particular personal emergency information and the AEI controller 147 follows this chain. The chain may be multiple steps such as from a) phone number to b) room number to c) user identifier of guest currently checked in to that room to d) personal emergency information associated with that user identifier; or the chain may be a single lookup operation such as when the target query information is the user identifier and the AEI controller 147 simply needs to retrieve the personal emergency information associated with that user identifier.

At step 512, the AEI controller 147 sends the personal emergency information retrieved from the AEI database 148 at step 510 to the PSAP controller 156 in response to the query from the PSAP controller 156.

At step 514, the PSAP controller 156 sends the personal emergency information to the operator console 154 for display. In this manner, the PSAP operator can answer the call and further sees the personal emergency information of the caller on operator console 154.

In the above-described example embodiments of FIG. 4 and FIG. 5, the AEI controller 147 (e.g., running on the cloud PBX server 120) dynamically keeps track of which emergency information is associated with which guest rooms as the guests check in and out of rooms. In this manner, the AEI controller 147 is ready to receive a query from the PSAP controller 156 at any time and is immediately able to reply to the query. However, other embodiments are possible which reduce the overhead on the AEI controller 147 when no emergency calls are made. For example, rather than the AEI controller 147 continually updating (storing and deleting) associations of user identifiers with guest rooms 112 of hotels 102 as different users check in and out of those hotel rooms 112, the AEI controller 147 may simply rely on the PMS 114 at each hotel to track this information during normal operations and only query the PMS 114 at a particular hotel 102a if an emergency call occurs and/or if a query from the PSAP controller 156 is received and the call was placed from that hotel 102a.

Figure 6:
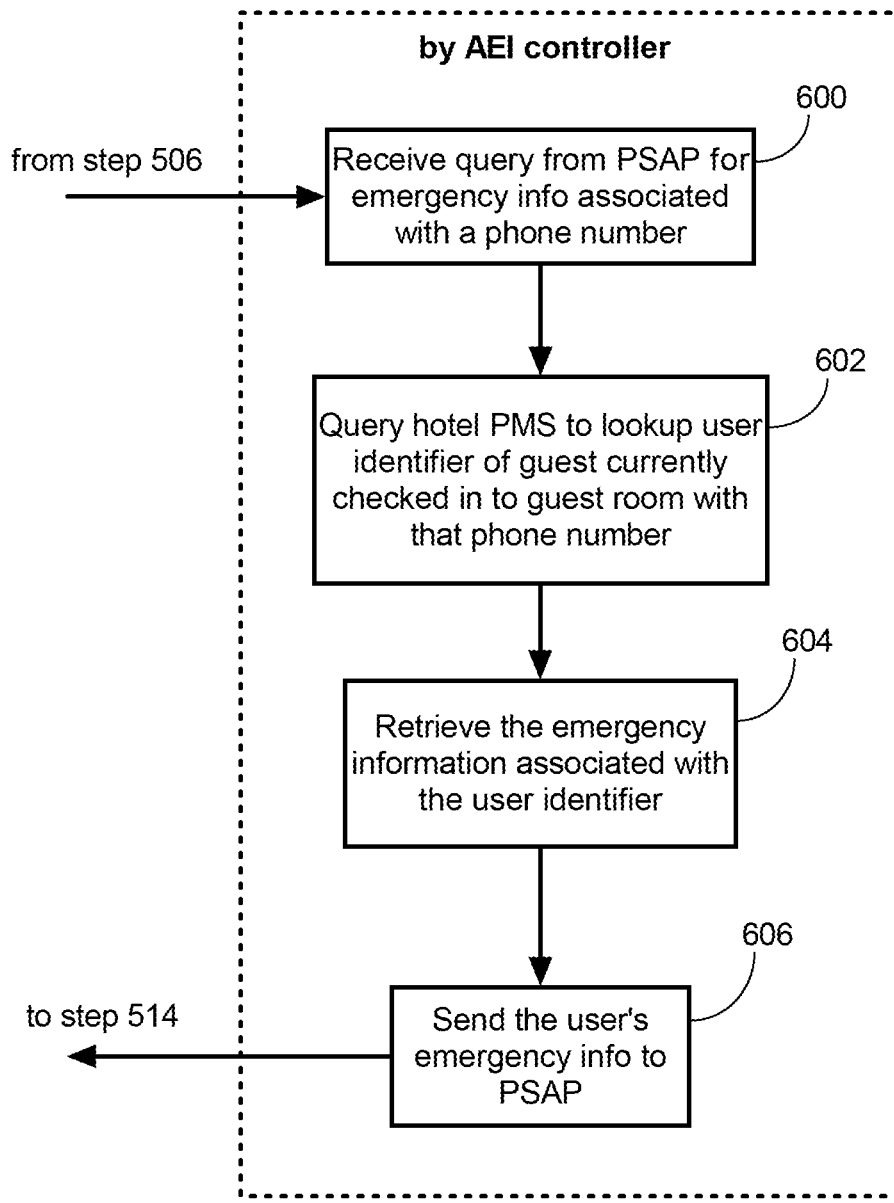
FIG. 6 illustrates a flowchart describing a method of providing personalized emergency information for emergency calls according to an exemplary embodiment of the invention.

FIG. 6 illustrates a flowchart describing a method of providing personalized emergency information for emergency calls according to an exemplary embodiment of the invention. In this embodiment, steps 408 and 416 of FIG. 4 are modified so that only the PMS 114 at the hotel stores and deletes records correlating user identifiers to guest rooms 112 as the guests check in and out of the hotel 102a. The AEI controller 147 is not informed of check-ins and check-outs as they happen in this embodiment. Instead, step 412 of FIG. 4 and FIG. 5 is replaced with the below-described steps performed by the AEI controller 147 shown in FIG. 6. Alternatively, the steps may be performed by another device different than the device specified below. The steps of the flowchart are not restricted to the exact order shown, and, in other configurations, shown steps may be omitted or other intermediate steps added. In this embodiment, the system 100 operates as follows:

At step 600, the AEI controller 147 receives the query from the PSAP controller 156. This step 600 is similar to as previously described for step 508 of FIG. 5.

At step 602, the AEI controller 147 queries the PMS 114 at the specific one of the hotels 102 that corresponds to the target query information received in the query from the PSAP controller 156. For example, the AEI controller 147 may receive a dedicated phone number (e.g., DID) of a particular guest room 112a at a particular hotel 102a. The AEI controller 147 then sends a request via the Internet 106 to the PMS 114 at that hotel to find the user identifier that is currently associated with that guest room 112a identified by that DID. In some embodiments, the request may be directly from the AEI controller 147 to the PMS 114; in other embodiments, the request may be indirect such as from the AEI controller 147 to the onsite PBX server 104 at the hotel, which stores a cached room list along with user identifiers of the currently checked in guests from the PMS 114.

At step 604, the AEI controller 147 searches the AEI database 148 to find the personal emergency information that corresponds to the user identifier obtained at step 602. This step may be similar to as previously described at step 510 of FIG. 5 except that instead of the AEI controller 147 finding the user identifier associated with the caller identifier information from its own records previously stored in the AEI database 148, the AEI controller 147 in this embodiment utilizes the user identifier retrieved from the PMS 114 at step 602.

At step 606, the AEI controller 147 sends the personal emergency information retrieved from the AEI database 148 at step 604 to the PSAP controller 156 in response to the query from the PSAP controller 156. This step corresponds to step 512 of FIG. 5.

As mentioned above, the PSAP controller 156 may query the AEI controller 147 at step 506 according to the source telephone number (i.e., the source caller ID) of the emergency call. This telephone number will correspond to the hotel room 112 from which the call was placed as long as the hotel 102 has a dedicated phone number associated with each guest room 112. However, since there are still legacy hotels that do not have a dedicated phone number for each guest room 112, in another embodiment of the invention, the onsite PBX server 104 and/or cloud PBX server 120 will add one or more identifier tags to the outgoing emergency call to assist the PSAP controller 156 in both performing location detection and obtaining personalized emergency information.

Figure 7:
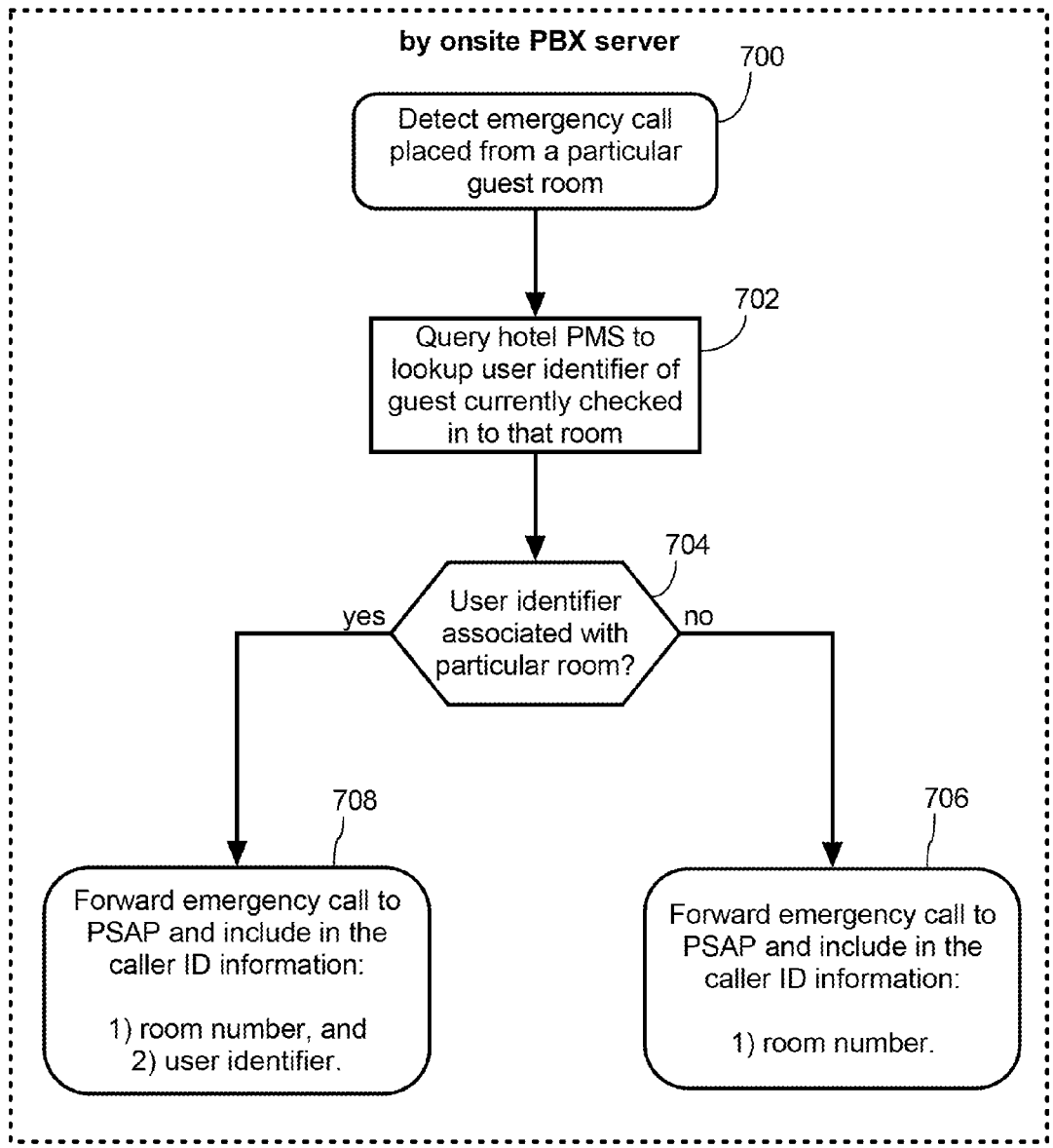
FIG. 7 illustrates a flowchart describing a method of providing personalized emergency information for emergency calls according to an exemplary embodiment of the invention.

FIG. 7 illustrates a flowchart describing a method of providing personalized emergency information for emergency calls according to an exemplary embodiment of the invention. In this embodiment, the illustrated steps are performed by an onsite computer server such as the onsite PBX server 104 at the hotel 102 from which the emergency call is placed. Alternatively, the steps may be performed by another device in other embodiments. The steps of the flowchart are not restricted to the exact order shown, and, in other configurations, shown steps may be omitted or other intermediate steps added. In this embodiment, the system 100 operates as follows:

At step 700, the onsite PBX server 104 at a hotel 102*a* detects that an emergency call has been placed from the in-room phone 108*a* of a particular guest room 112*a*. Similar to as previously described this step may be performed by the onsite PBX server 104 examining the destination phone number and finding that it matches 9-1-1 or another predetermined number corresponding to emergency services.

At step 702, the onsite PBX server 104 queries the PMS 114 at the hotel 102 to lookup whether there is user identifier for the guest currently checked in to the room 112*a* from which the emergency call was placed.

Each room 112 in the hotel has a different phone extension (e.g., extension "101" for "Room 101", extension "103" for "Room 103" etc.) and the onsite PBX server 104 can see the source extension number of the call and thereby determine (or lookup in a room extension database) the corresponding room number. The onsite PBX server 104 queries the PMS 114 to get a report of the guest details for the guest who is currently checked in to the room 112*a* from which the call was placed. The onsite PBX server 104 may query the PMS 114 in real time in response to detecting the emergency call, or, in other embodiments, the onsite PBX server 104 may periodically query the PMS 114 to get an updated room list having the details for all the rooms and cache this information in a storage device within the onsite PBX server 104. In yet other embodiments, the PMS 114 may send check-in and checkout-messages in response to guests checking in and out, or otherwise push the room assignment information to the onsite PBX server 104 via hotel LAN 110.

At step 704, the onsite PBX server 104 determines whether there is a user identifier currently associated with the particular room 112*a* from which the emergency called was placed. As previously described, when the room 112*a* is vacant, there will be no valid user identifier associated with that room 112*a*. Likewise, some guests may not participate in the hotel's loyalty program and therefore when such a guest is checked in to the room 112*a* there will not be any user identifier stored in the PMS 114 associated with the room even though the room is occupied. When there is a user identifier associated with the particular room 112*a* from which the emergency call was placed control proceeds to step 706; otherwise, control proceeds to step 708.

At step 706, the onsite PBX server 104 forwards the emergency call to the PSAP controller 147 (e.g., via the Internet 106, the cloud PBX server 120, and/or the telecom phone network 118). In this example, the source phone number on the outgoing call indicates the hotel's main phone number because the hotel does not have a DID for each guest room. However, in the name field of the caller ID information for the call, the onsite PBX server 104 includes location information indicating the particular hotel room 112*a* from which the emergency call was placed. As there is currently no user identifier associated with that room 112*a* (i.e., the "no" branch of step 704), the onsite PBX server 104 does not include any user identifier information in the name field of the caller ID for the outgoing emergency call.

At the PSAP, the PSAP controller 156 receives the emergency call and displays to the PSAP operator on console 154 both the hotel room number specified in the name field of the caller ID information along with the hotel's name and address (i.e., retrieved from the ALI database 158 at step 502 of FIG. 5 according to the hotel's main phone number in the number field of the source caller ID). In this embodiment, because there is no user identifier specified in the name field of the caller ID information for the incoming call, the PSAP controller 156 does not query the AEI controller 147 (e.g., skip steps 506, 508, 510, 512 and 514 of FIG. 5); however, in other embodiments the PSAP controller 156 still queries the AEI controller 147 using the hotel room number specified in the name field of the caller ID information as the target query in step 506. Regardless, even if there is no emergency information available for the caller, beneficially, the PSAP operator is still automatically made aware of the hotel's name and address along with the specific guest room number within the hotel from which the emergency call was placed. This occurs even though the hotel does not employ a unique source phone number (e.g., a DID) for calls made from the in-room phones 108 in each hotel room 112*a* and instead uses the hotel's main phone number as the source number field for all outgoing calls.

At step 708, the onsite PBX server 104 forwards the emergency call to the PSAP controller 147 (e.g., via the Internet 106, the cloud PBX server 120, and/or the telecom phone network 118). As described above for step 706, the source phone number on the outgoing call indicates the hotel's main phone number because the hotel does not have a dedicated number (e.g., DID) for each guest room 112.

However, in the name field of the caller ID information for the call, the onsite PBX server 104 includes both location information indicating the particular hotel room 112*a* from which the emergency call was placed along with the user identifier associated with the currently checked in guest of that room 112*a* as retrieved from the PMS 702 at step 702.

As a result, the PSAP controller 156 receives the emergency call and displays to the PSAP operator on console 154 both the hotel room number specified in the name field of the caller ID information along with the hotel's name and address (i.e., retrieved from the ALI database 158 at step 502 of FIG. 5 according to the hotel's main phone number in the number field of the caller ID). Further, because there is also a user identifier specified in the name field of the caller ID information for the incoming call, the PSAP controller 156 also queries the AEI controller 147 (e.g., at step 506 of FIG. 5) using the specified user identifier as the target query information to request any associated personal emergency information. Thus, in this embodiment, the PSAP operator is automatically made aware of the hotel's name and address, the specific guest room number within the hotel from which the emergency call was placed, and any personal emergency information that is associated with the guest currently checked in to that room.

In another embodiment, rather than using the user identifier specified in the name field of the caller ID as the target query to the AEI controller 147, the PSAP controller 156 queries the AEI controller 147 (e.g., at step 506 of FIG. 5) using the room number as the target query information to request any associated personal emergency information. In this case, the user identifier included the name field of the caller ID information simply acts as a flag to tell the PSAP controller 156 that emergency information may be available and to make the query to the AEI controller 147 at step 506. Any other fixed or changing flag value rather than a user identifier could be inserted by the onsite PBX server 104 and recognized by the PSAP controller 156 to achieve this purpose.

Figure 8:
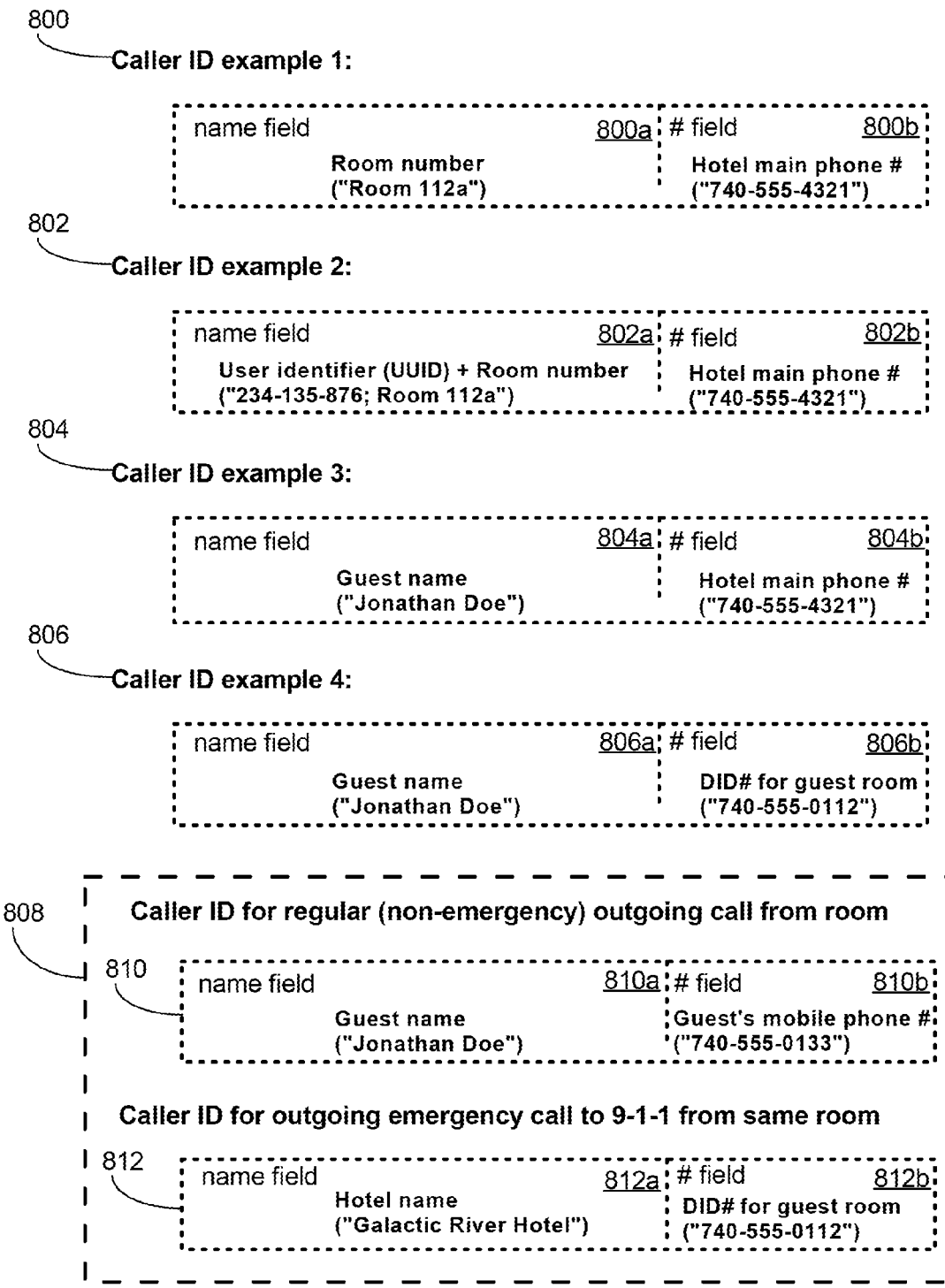
FIG. 8 illustrates several examples of how the onsite PBX server of FIG. 1 may populate the caller ID information fields of the outgoing emergency call to include location information, user identifier tags, and other information.

A typical caller ID field has a name field of up to about 20 alphanumeric characters and a number field of up to about 11 numerical digits. FIG. 8 illustrates several examples of how the onsite PBX server 104 may populate the caller ID information fields of the outgoing emergency call to include location information, user identifier tags, and other information. For example, at steps 706 and/or 704 of FIG. 7 the onsite PBX server 104 may populate the caller ID fields of the outgoing emergency call in one or more of the manners shown. Similar techniques may also be employed by the onsite PBX server 104 or cloud PBX server 120 of a hotel 102*a* that does have a dedicated phone number (DID) for each guest room 112.

In a first caller ID example 800, the onsite PBX server 104 inserts the room number from which the call was placed in the name field 800*a* and inserts the hotel's main phone number in the number field 800*b*. This example may correspond to step 704 of FIG. 7 where there is no user identifier currently associated with the room 112*a* from which the emergency call was placed or may correspond to another embodiment where the PSAP controller 156 will always query the AEI controller 147 at step 506 using the room number as the target query information. The hotel main phone number in the number field 800*b* enables the PSAP controller 156 to lookup the name and address of the hotel (from the ALI database 158), and the room number in the name field 800*a* allows the PSAP operator to see where in the hotel the caller is located, and to query the AEI controller 147 for any personal emergency information associated with that room 112*a*.

In a second caller ID example 802, the onsite PBX server 104 inserts both the room number from which the call was placed and the unique user identifier (UUID) for the guest currently checked in to that room 112*a* in the name field 802*a*; and inserts the hotel's main phone number in the number field 802*b*. This example may correspond to step 706 of FIG. 7 where there is a user identifier stored in the PMS 114 for the currently checked in guest of the room 112 from which the emergency call was placed. The hotel main phone number in the number field 800*b* enables the PSAP controller 156 to lookup the name and address of the hotel (from the ALI database 158), and allows the PSAP operator to see where in the hotel the caller is located. The user identifier in the name field 800*a* indicates that personal emergency information may be available from the AEI database 148 and can be used as the target query information to the AEI controller 147 at step 506 to see if there is any personal emergency information associated with that user identifier.

In a third caller ID example 804, the onsite PBX server 104 inserts the name of the guest who is currently checked in to the room from which the emergency call is placed in the name field 804*a* and inserts the hotel's main phone number in the number field 804*b*.

The onsite PBX server 104 finds the name of the guest staying the room 112*a* by querying the PMS 114 after an emergency call is placed or by caching the PMS 114 room information before the call is placed.

Upon receiving the emergency call, the PSAP controller 156 displays to the operator on console 154 the name of the guest (name field of source caller ID) and the name and address of the hotel (looked up from the ALI database 158 according to the hotel's main phone number received in the caller ID info). The PSAP controller 156 also queries the AEI controller 147 using both the hotel main phone number and the guest's name as the target query to see whether there is any personal emergency information associated with this combination of guest and hotel names. The AEI controller 147 queries the PMS 114 at the hotel 102*a* that corresponds to that phone number to find out if there is a guest currently checked in with that name. If yes, the PMS 114 will return the guest's assigned room number and possible the user's identifier. The room number is sent to the PSAP controller 156 for display to the PSAP operator handling the call. Further, the AEI controller 147 searches the AEI database 148 and if there is any personal emergency information associated with that user's name and/or user identifier then this information is also sent to the PSAP controller 156 for displayed to the PSAP operator handling the call.

In a fourth caller ID example 806, the onsite PBX server 104 inserts the name of the guest who is currently checked in to the room from which the emergency call is placed in the name field 806*a* and inserts the dedicated phone number (e.g., DID) for the that guest room 112*a* in the number field 806*b*.

Similar to as described above, the onsite PBX server 104 finds the name of the guest by checking room assignment information from the PMS 114 after an emergency call is placed.

Upon receiving the emergency call, the PSAP controller 156 displays to the operator on console 154 the name of the guest (name field of source caller ID) and the name, address, and room number of the hotel (looked up from the ALI database 158 according to the dedicated phone number for that guest room 112a received in the caller ID info). The PSAP controller 156 also queries the AEI controller 147 using the dedicated phone number of the guest room 112a as the target query to see whether there is any personal emergency information currently associated with this guest room 112a. The AEI controller 147 queries the PMS 114 and/or the AEI database 148 to find the user identifier associated with the target room number and then to find any personal emergency information associated with that user identifier. Alternatively, in another embodiment, the personal emergency information may be directly associated with the guest room 112a while the user is checked in to that room 112a. In this case, the AEI controller 147 queries the AEI database 148 to directly find any personal emergency information currently associated with the target hotel room 112a according to its room number or DID.

An example of selective outgoing caller ID values for emergency and non-emergency calls is shown in the bottom box 808 of FIG. 8. In this example, the onsite PBX server 104 inserts different caller ID information for emergency calls made from an in-room phone 108a of a particular guest room 112a and regular (non-emergency) calls made from that same in-room phone 108a. This feature is works together with the custom outgoing call rules described in U.S. provisional patent application No. 61/910,858 filed on Dec. 2, 2013 and entitled "HOSPITALITY PRIVATE BRANCH EXCHANGE (PBX) SYSTEM WITH DYNAMIC RULES FOR COMPLEMENTING MOBILE PHONES OF CURRENTLY CHECKED IN GUESTS", the contents of which being incorporated herein by reference.

While the user of mobile phone 124 is checked in to room 112a and makes non-emergency outgoing calls (i.e., to destination phone numbers other than 9-1-1), the onsite PBX server 104 inserts caller ID values as shown in example 810 in FIG. 8. In particular, the onsite PBX server 104 inserts the guest's name in the name field 810a and inserts the phone number of the guest's personal mobile phone 124 in the number field 810b. As explained in the above-referenced app. No. 61/910,858, a benefit of this is that when an external phone receives the call it will behave as if the user had called from mobile phone 124. Address book functionality, call back functionality, distinct rings etc. will work as expected.

However, as shown in caller ID example 812 in FIG. 8, when the user makes an emergency call (e.g., to destination phone number of 9-1-1 and/or any other predetermined emergency phone numbers), the onsite PBX server 104 ignores the user's custom outgoing call rule and inserts the name of the hotel in the name field 812a and the dedicated phone number (e.g., DID) for the guest room 112a from which the call was placed within the hotel 102a. A benefit of populating the phone number of the guest room 112 rather than the phone number of the user's mobile phone 124 in the source caller ID information for an outgoing emergency call includes allowing the PSAP controller 156 to accurately determine the location of the caller by querying the ALI database according to the dedicated number of the guest's assigned room 112a. Further, the AEI controller 146 may also send personal emergency information to the PSAP controller using any combination of the examples provided above.

In this way, the outgoing caller ID rule may be automatically canceled by the onsite PBX server 104 or the cloud PBX server 120 in the event the destination phone number is 9-1-1. In this manner, the PSAP controller 156 will see the dedicated phone number of the guest's room as the source caller ID of the incoming emergency call and is able to properly perform automatic location detection by looking up the source phone number in the ALI database 158.

In another example (not shown), the onsite PBX server 104 inserts the name of the hotel from which the call was placed in the name field and inserts the dedicated phone number (e.g., DID) for the specific guest room 112a from which the emergency call was placed in the number field. This example is useful because minimal functionality is required by the onsite PBX server 104 for outgoing calls. For example, calls made from a legacy onsite PBX server may include this standard caller ID information for all calls placed from in-room phones room 108.

Figure 9:
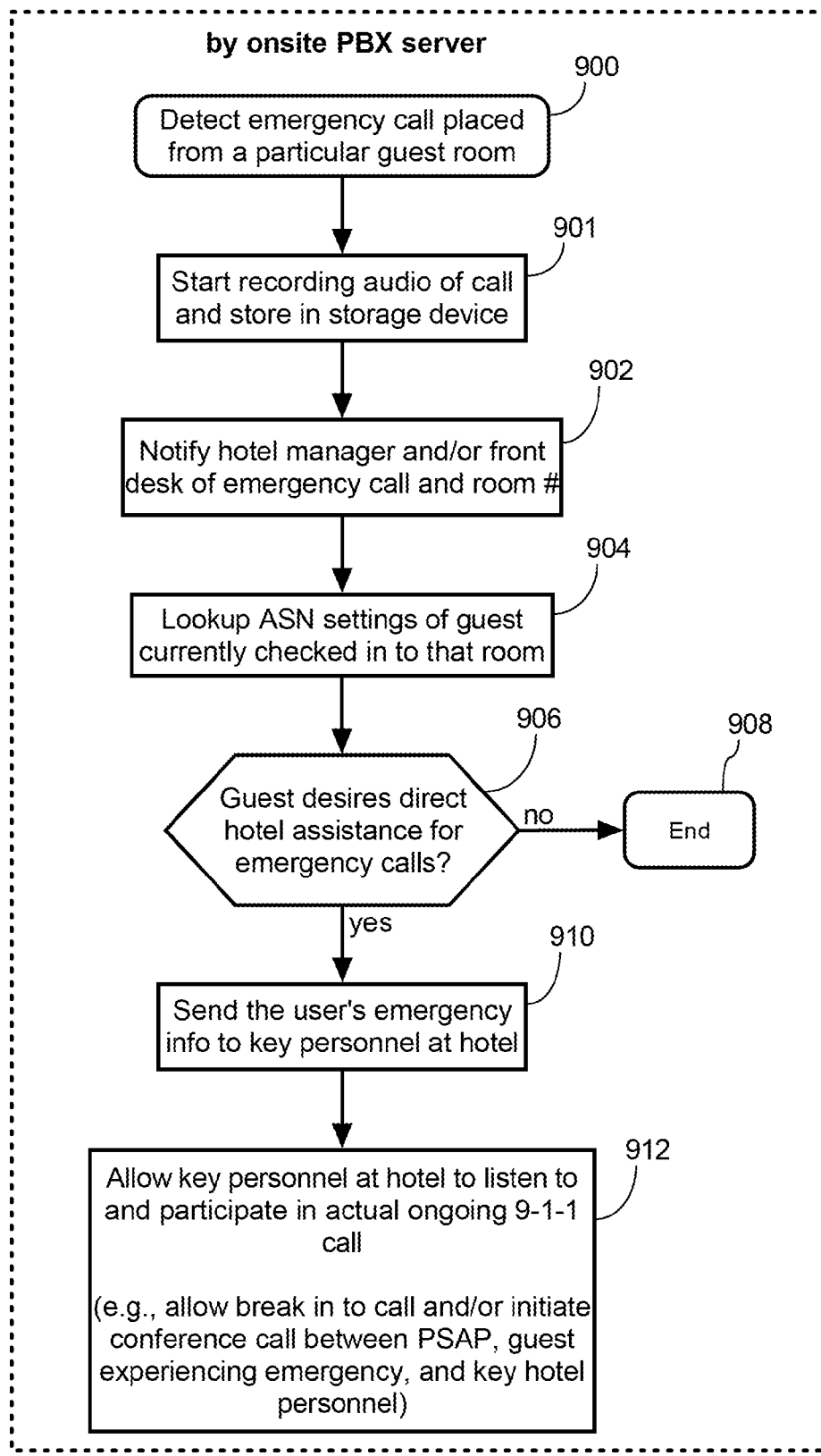
FIG. 9 illustrates a flowchart describing a method of providing personalized emergency information for emergency calls according to an exemplary embodiment of the invention.

FIG. 9 illustrates a flowchart describing a method of providing personalized emergency information for emergency calls according to an exemplary embodiment of the invention. In this embodiment, the illustrated steps are performed by an onsite computer server such as the onsite PBX server 104 at the hotel 102 from which the emergency call is placed. Alternatively, the steps may be performed by another device in other embodiments.

In an embodiment, the steps of the flowchart in FIG. 9 are carried out in parallel with the steps of the flowchart in FIG. 7. FIG. 7 deals with the onsite PBX server 104 connecting the emergency call to PSAP 150 whereas FIG. 9 deals with the onsite PBX server 104 notifying key hotel personnel of the emergency call as it is placed. The steps of the flowchart in FIG. 9 are not restricted to the exact order shown, and, in other configurations, shown steps may be omitted or other intermediate steps added. In this embodiment, the system 100 operates as follows:

At step 900, the onsite PBX server 104 at a hotel 102a detects that an emergency call has been placed from the in-room phone 108a of a particular guest room 112a. This step may be performed by the onsite PBX server 104 examining the destination phone number of an outgoing call and finding that it matches 9-1-1 or another predetermined number corresponding to emergency services.

At step 901, the onsite PBX server 104 begins recording all audio on the call between the caller (e.g., the guest calling 9-1-1 at the hotel) and the operator at the PSAP 150 handling the emergency call. The onsite PBX server 104 may connect the call to the PSAP controller 156 using the steps FIG. 7 or any other process such as simply forwarding the call without doing anything special to the caller ID information. However, in this embodiment, the onsite PBX server continues to monitor the call and records (e.g., stores) the audio as the call progresses in a file in the audio storage device 115. In addition to being located onsite at the hotel, the audio storage device 115 may also be located in the cloud such as integrated with the cloud PBX server 120 in other embodiments.

At step 902, the onsite PBX server 104 notifies one or more key personnel at the hotel 102b of the emergency call. Examples of key personnel include the hotel manager, front desk staff, the hotel owner, and onsite medical staff. The onsite PBX server 104 may notify these key personnel by calling them on their predetermined mobile phone numbers, a list of which are stored on a storage device within the onsite PBX server 104. In other embodiments, the onsite PBX server 104 may send SMS, MMS, and/or e-mail messages to the key personnel via the predetermined mobile phone numbers, email addresses, pager numbers, etc.

At step 904, the onsite PBX server 104 queries the PMS 114 at the hotel 102 to lookup whether there is a user identifier for the guest currently checked in to the room 112a from which the emergency call was placed. As previously described, each room 112 in the hotel 102a has a different phone extension (e.g., extension "101" for "Room 101", extension "103" for "Room 103" etc.) and the onsite PBX server 104 can see the source extension number of the call and thereby determine (or lookup in a room extension database) the corresponding room number. With this room number, the onsite PBX server 104 queries the PMS 114 at the hotel to retrieve the user identifier (e.g., hotel rewards program membership number) for the guest currently checked in to the room. Assuming the room is occupied by a guest with a user identifier, the onsite PBX server 104 retrieves that user's ASN settings from the user profile database 109 and/or the AEI database 148 according to the user identifier. As previously explained with regard to FIG. 2, the user's ASN settings were previously stored by the user when joining the rewards program or anytime thereafter. The onsite PBX server 104 can find the user's ASN settings by matching the user identifier for the registered guest of the room in the PMS 114 with the user identifier of the user's ASN settings (e.g., previously entered by user at field 202 of the ASN settings in FIG. 2).

At step 906, if the user's ASN settings retrieved at step 904 indicate that the user desires direct hotel assistance for emergency calls (i.e., setting 209 in FIG. 2 is "yes"), control proceeds to step 906; otherwise, the process ends without further hotel staff participation (step 908). In the latter, the caller is connected to the PSAP 150 via the process previously described in FIG. 7 and hotel management/front desk are aware of the call but are not otherwise involved. The audio recording started at step 901 may also be automatically terminated and deleted by the onsite PBX server 104 at step 908 to protect the guest's privacy.

At step 910, because the user's ASN settings retrieved at step 904 indicate that the user does desire direct hotel assistance for emergency calls (i.e., setting 209 in FIG. 2 is "yes"), the onsite PBX server 104 sends the user's personal emergency information to the key personnel at the hotel 102*a*. The process of sending the user's personal emergency information to key personnel at the hotel 102*a* may be done similar to any of the above described methods for sending the emergency info to the PSAP 150 (e.g., step 310 of FIG. 3, step 412 of FIG. 4, step 512 of FIG. 5, and/or step 606 of FIG. 6). This includes the onsite PBX server 104 pushing (e.g., sending/transmitting/forwarding) the emergency info such as via e-mail or MMS messages to the mobile phones or other digital assistants, computers, or other predetermined addresses utilized by the key personnel at the hotel.

In some embodiments, the key personnel to which the info will be sent are fixed for all emergency calls where the guest desires hotel assistance. In other embodiments, the key personnel may be dynamically selected by the onsite PBX server 104 according to the user's ASN settings and/or the guest's personal emergency information. For example, a guest who is awaiting treatment for a particular condition may desire that their doctor or another key person or destination also be automatically be notified and allowed to participate in any emergency call that the user makes.

At step 912, the onsite PBX server 104 allows the key personnel who are to assist the guest with the emergency call to listen to and participate in the actual ongoing emergency call. In an exemplary embodiment, this is done by the onsite PBX server 104 calling the key personal on their mobile phones and playing an audio message such as:

"This is the Advanced Safety Notification system, room 809 has just placed a 9-1-1 call. To hear chronological information about this call press 1, to hear a recording of the start of the 9-1-1 call press 2. At any time, press 3 to join the live emergency call 9-1-1 in progress."

Taking the hotel manager as an example, upon receiving the above notification call from the onsite PBX server 104, if the manager presses 1, the onsite PBX server 104 verbally provides room information, time stamps of the call, a duration of the call and information on whether the call is still ongoing or has been terminated. If the hotel manager presses 1, the onsite PBX server 104 plays back the full recording of the call as stored in the audio storage device 115. In this way, the manager can hear the starting of the call and everything afterwards but will not be listening to the live call. If the hotel manager presses 3, the onsite PBX server 104 will join the ongoing emergency call to the manager's notification call. In this way, the onsite PBX server 104 creates a three-caller conference call between the guest experiencing the emergency, the PSAP operator who answered the 9-1-1 call, and the hotel manager who received the notification call alerting him of what is happening. All parties on the conference call may speak and be heard. Later, if another key hotel personnel such as an onsite nurse presses 3 while listening to his/her notification call, the onsite PBX server 104 will add that party in to the conference and it will become a four-caller conference call. Any number of the key personnel notified of the guest's personal emergency info at step 910 may join and participate in the ongoing emergency call. Likewise, if a party hangs up or is disconnected, the remaining parties will still be on the conference call. In this manner, even if the guest who originated the 9-1-1 call hangs up or is inadvertently disconnected, the PSAP operator and the key hotel personnel may continue to discuss the situation. This may be beneficial as the key personnel at the hotel will often be able to reach the guest faster than any other EMS dispatched by the PSAP operator.

As described, multiple personnel can be notified simultaneously of the 9-1-1 call and join the conference call dynamically created by the onsite PBX server 104. This is especially helpful in large disaster situations like a fire, flood, shooting, etc.

In another embodiment, rather than performing emergency information look-up at step 506 of FIG. 5 according to the phone number field of the source caller ID, the PSAP controller 156 performs emergency information lookup according to the user's identifier (or other identifying information) in the name field of the source caller ID. For example, the target query information in step 506 of FIG. 5 queried by the PSAP controller 156 may be the user's identifier found in the name field of the caller ID on the incoming emergency call.

FIG. 10 shows example caller ID values for emergency calls. In the top portion, example caller ID 1000 represents the values as populated by the onsite PBX server 104 or the cloud PBX server 120 when an outgoing emergency call is made at the hotel 102*a* from a guest's room 112*a* and the user has selected to make their personal emergency information available to the PSAP 150. (i.e., "yes" setting 208 in FIG. 2) The onsite PBX server 104 inserts the unique user identifier (UUID) associated with the guest currently checked in to the room from which the emergency call was placed in name field 1000*a*; and inserts the dedicated phone number (e.g., DID) for that guest room 112*a* in the number field 1000*b*. The user's unique identifier is retrieved by the onsite PBX server 104 from PMS 114, for example, or may be retrieved by the onsite PBX server 104 correlating the checked in guest with a particular account in the AEI database 148.

Upon receiving the emergency call at the PSAP 150, the dedicated phone number of the guest room in the number field 1000*b* enables the PSAP controller 156 to lookup the name and address of the hotel along with the particular guest room number from the ALI database 158 at step 502 of FIG. 5. The user identifier in the name field 1000a indicates that personal emergency information may be available from the AEI database 148 and is used as the target query information by the PSAP controller 156 to the AEI controller 147 at step 506.

Example caller ID 1002 represents the values as populated by the user's mobile phone 124 or another telecom provider device when an emergency call is made from the user's mobile phone 124. By the user configuring their mobile phone 124 (or another telecom provider device such as a website allowing residential ASN configuration settings similar to FIG. 2) with the user's identifier, upon an emergency call placed from the user's phone 124, the name field 1002a of the emergency call is populated with the user's identifier.

By the user's mobile phone 124 and/or the telecom provider device populating the caller ID fields as shown in example 1002 for an emergency call placed from the user's mobile phone 124, the PSAP controller 150 can retrieve and display the user's personal emergency information as correlated to the user's identifier in the same manner as described above for calls made from the guest's hotel room 112a. For example, the PSAP controller 150 determines the location of the caller using any acceptable method, e.g., by searching the ALI database 158 and/or performing cell tower 122 triangulation according to the phone number of the user's mobile device 124 in number field 1002b. Likewise, the user identifier in the name field 1002a indicates to the PSAP controller 156 that personal emergency information may be available from the AEI database 148 for this caller, and is used by the PSAP controller 156 as the target query information to the AEI controller 147 at step 506.

A benefit of this embodiment is that the PSAP controller 156 operates the same way regardless of the source of the incoming emergency 9-1-1 call; in particular, the phone number field of the incoming emergency call's caller ID may be utilized by the PSAP controller 156 to determine the location of the caller and the user identifier in the name field of the caller ID of the incoming emergency call is utilized by the PSAP controller 156 to retrieve any personal emergency information associated with the caller from the AEI database 148. Residential emergency calls, mobile phone emergency calls, business emergency calls, hotel guest room emergency calls, etc. are all handled by the PSAP controller 156 in the same manner.

In this embodiment, the user's identifier included in the name field 1000a, 1002a of the caller ID information for the emergency call acts similar to a medical alert identifier for the caller. Medical information (or other personal emergency information) for the user stored in the AEI database 148 is correlated to the user's identifier. The PSAP controller 156 can thereby utilize the user's identifier received in the caller ID for an incoming emergency call to query the AEI controller 147 and/or AEI database 148 and obtain that caller's medical details (or other personal emergency information).

In some situations it may be beneficial to allow the caller making a 9-1-1 call to make a decision of whether to send their personal emergency information at the time the 9-1-1 call is actually placed. For example, when a user is making a 9-1-1 call because they are themselves experiencing an emergency they may want to provide PSAP 150 with their personal emergency information. However, when the user is making a 9-1-1 call in order to report an emergency experienced by another person, for example, when the user witnesses a traffic accident, the user may not want to provide PSAP 150 with the user's own personal emergency information because it is not relevant to the actual emergency taking place.

Figure 11:
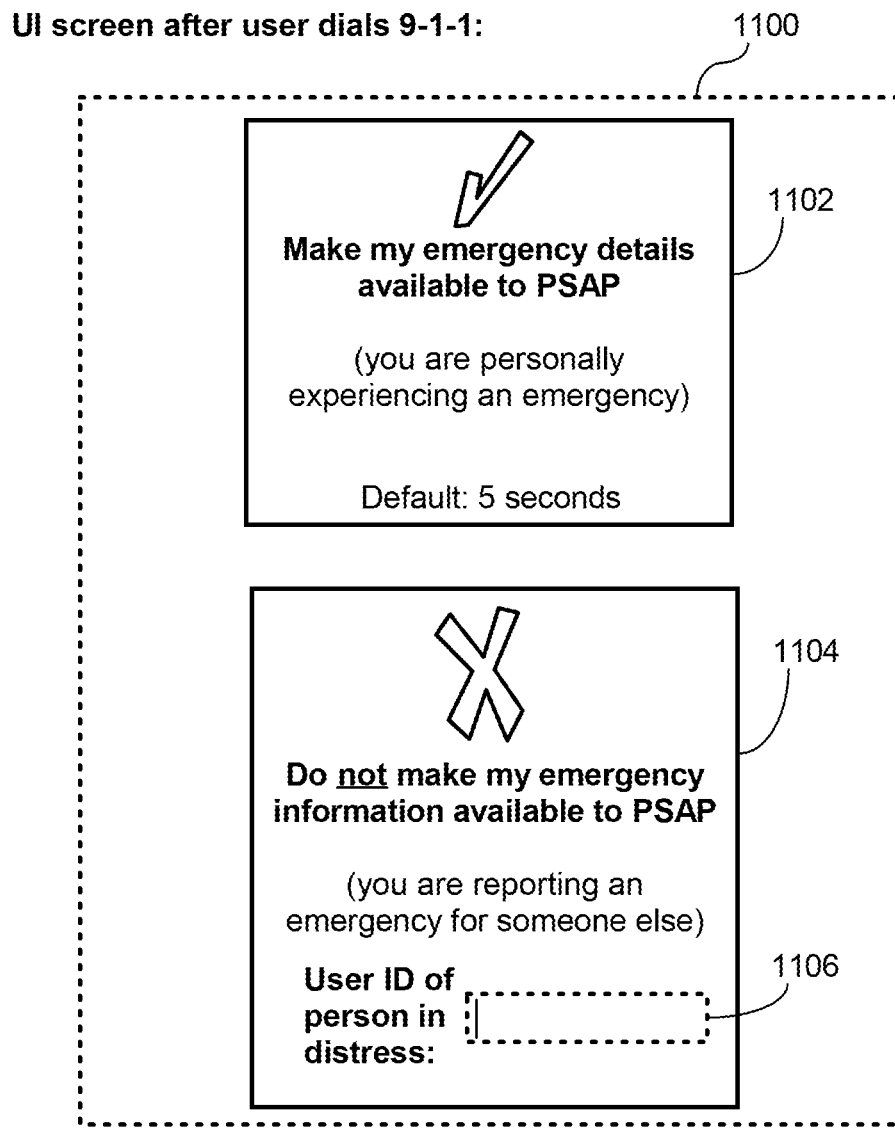
FIG. 11 illustrates a user interface (UI) screen presented to the user when making an emergency call according to an exemplary embodiment of the invention.

FIG. 11 illustrates a user interface (UI) screen 1100 presented to the user when making an emergency call. UI screen 1100 allows the user to decide whether or not to make their personal emergency information available to the PSAP 150 and/or key hotel personal assisting with the emergency call. UI screen 1100 may be displayed to the user on a UI interface such as a touchscreen on an in-room phone 108 and may also be displayed on the user's mobile phone 124 upon the user dialing 9-1-1 from their own phone 124 regardless of whether the user is currently checked into a hotel 102.

An application running the in-room phone 108 or the user's phone 124 may detect that an emergency call is being placed and then display UI screen 1100 immediately afterwards on a touchscreen built in to the phone 108, 124. One or more processors within the phone 108, 124 may execute the application as loaded from a storage medium such as a FLASH memory device or other non-volatile storage device coupled thereto. In another embodiment, the application program may be executed by one or more processors on the onsite PBX server 104 or another telecom device or server on telecom network 118 operating in conjunction with the in-room phone 108 or the user's mobile phone 124 as the case may be.

After being presented with UI screen 1100, the user decides whether to make their personal emergency information available to the PSAP 150 (and/or key hotel personal or other destinations) for the emergency call. In some embodiments, rather than preset configurations such as fields 208 and 209 in the ASN settings of FIG. 2, the user dynamically decides at the time of the call whether to provide their emergency information by selecting one of option 1102 or option 1104 on UI screen 1100. Alternatively, the user may still setup preconfigured settings such as the setting fields 208 and 209 shown in FIG. 2 and these settings correspond to the default action of the application program on the phone, but the user may manually override the preconfigured default at the time is placed.

The first option 1102 is configured as the default in this example and will automatically be selected by the phone 108, 124 after 5 seconds if the user makes no manual override selection when placing a 9-1-1 call. Assuming the user is making a 9-1-1 call from their in-room phone 108a and that the first option 1102 of UI screen 1100 is selected (either automatically by default or manually by the user), the onsite PBX server 104 receives an indication of the selection from the in-room phone 108a and in response populates the outgoing caller ID fields as shown in example 1000 in FIG. 10 so that the UUID of the user currently checked in the to the guest room 112a from which the call was placed is included in the name field 1000a. The fact that the user's identifier is included in the name field 1000a indicates to the PSAP controller 156 that emergency information may be available for this call. The PSAP controller 156 therefore queries the AEI controller 147 using the user's identifier as the target query information (step 506 of FIG. 5) in order to retrieve any personal emergency information associated with that user identifier in the AEI database 148.

Alternatively, when the user is making the 9-1-1 call from their in-room phone 108a but the second option 1104 is selected, the onsite PBX server 104 receives an indication of the selection from the in-room phone 108a and in response populates the outgoing caller ID fields as shown in example 1004 in FIG. 10 so that only the name of the user currently checked in to the guest room 112*a* from which the call was placed is included in the name field 1004*a*. The fact that there is no user identifier in the name field 1004*a* indicates to the PSAP controller 156 that emergency information is not available for this call. The PSAP controller 156 therefore does not query the AEI controller 147; i.e., steps 506, 508, 510, 512, and 514 of FIG. 5 are omitted.

In another example, assuming the user is making a 9-1-1 call from their personal mobile phone 124 and that the first option 1102 of UI screen 1100 is selected, a telecom server on telecom phone network 118 that is handling the call receives an indication of the selection from the mobile phone 124 and in response populates the caller ID fields as shown in example 1002 in FIG. 10 so that the UUID of the user to which the mobile phone 124 belongs is included in the name field 1002*a*. The fact that the user's identifier is included in the name field 1002*a* indicates to the PSAP controller 156 that emergency information may be available for this call. The PSAP controller 156 therefore queries the AEI controller 147 using the user's identifier as the target query information (step 506 of FIG. 5) in order to retrieve any personal emergency information associated with that user identifier in the AEI database 148.

Alternatively, when the user is making the 9-1-1 call from their personal mobile device 124 but the second option 1104 of UI screen 1100 is selected, the telecom server handling the call receives an indication of the selection from the mobile phone 124 and in response populates the caller ID fields as shown in example 1006 in FIG. 10 so that only the name of the user to which the mobile phone 124 is registered is included in the name field 1006*a*. The fact that there is no user identifier in the name field 1006*a* indicates to the PSAP controller 156 that emergency information is not available for this call. The PSAP controller 156 therefore does not query the AEI controller 147; i.e., steps 506, 508, 510, 512, and 514 of FIG. 5 are omitted.

In yet another embodiment, an input field 1106 is included for the second option 1104 so that the user may input the user identifier associated with the emergency call. For example, the mobile phone 124 may be carried by a staff member at the hotel 102*a*. The staff member may encounter a guest who is experiencing an emergency and utilize mobile phone 124 to call 9-1-1 for the guest, and at UI screen 1100 the staff member enters the user identifier of the guest experiencing the emergency in input filed 1106 and then selects option 1104. This will cause the onsite PBX server 104 or the telecom server handling the call to populate the UUID entered at field 1106 in the name field of the caller ID information.

The caller making the emergency call may determine the user identifier of the person experiencing the emergency in any suitable manner. In one example, the caller may happen upon an unconscious person and see that that person is wearing a medical alert ID tag on their wrist that indicates their user identifier. Other input fields (not shown) may also be displayed on UI screen 1100 to allow the person making the 9-1-1 call to specify other information regarding the emergency, for example, a location identifier field may be employed so that the caller can input the hotel room number, which is passed to PSAP 150 via the name field of the caller ID information on the emergency call in a similar manner. A room number field may allow the caller to enter a hotel room, which is then correlated with a particular user ID for transmission to the PSAP by the onsite PBX server 104 possibly working in tandem with the hotel PMS 114.

Figure 12:
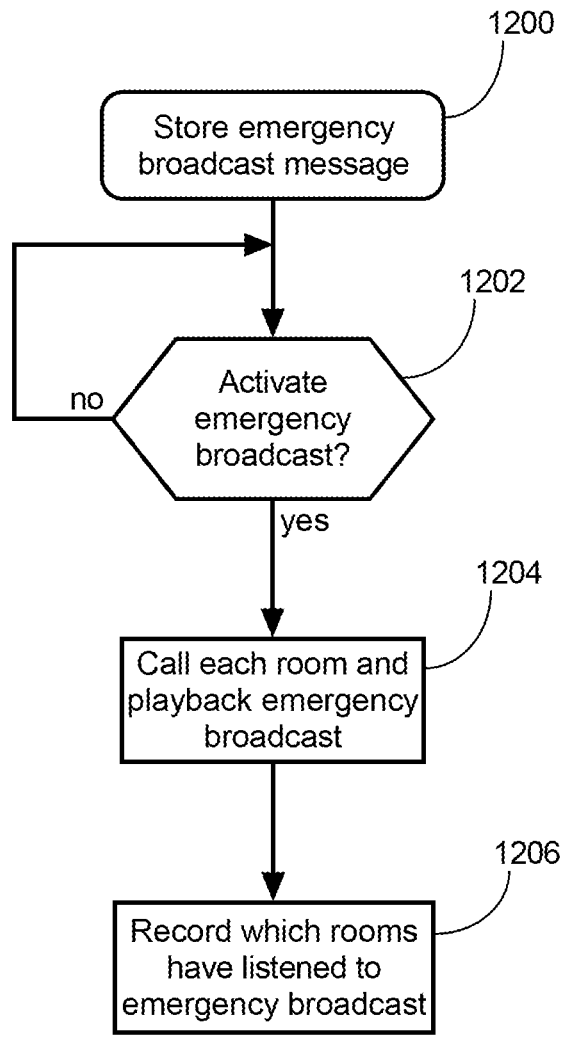
FIG. 12 is a flowchart describing a method of providing a reverse 9-1-1 emergency broadcast message according to an exemplary embodiment of the invention.

FIG. 12 is a flowchart describing a method of providing a reverse 9-1-1 emergency broadcast message according to an exemplary embodiment of the invention. In this embodiment, the illustrated steps are performed by an onsite computer server such as the onsite PBX server 104 at the hotel 102 from which the emergency call is placed. Alternatively, the steps may be performed by another device such as the cloud PBX server 120 in other embodiments. The steps of the flowchart are not restricted to the exact order shown, and, in other configurations, shown steps may be omitted or other intermediate steps added. In this embodiment, the system 100 operates as follows:

At step 1200 a hotel manager or other person affiliated with hotel 102*a* records an emergency broadcast. In this embodiment, the emergency broadcast is a verbal telephone message which is stored by the onsite PBX server 104 in the audio storage device 115. However, other types of emergency messages may be employed in other embodiments such as audio/visual messages and/or text messages. In an usage example, the hotel 102*a* may receive a call from the local police department that an armed situation is unfolding across the street from the hotel 102*a*. The hotel manager then in turn accesses the onsite PBX server 104, enters his or her password and provides a message warning guests to stay in their rooms 112 or use the back entrance only. The manager may access the onsite PBX server 104 by dialing a predetermined extension from his mobile phone 124, any in-room phone 108 or from a front desk phone.

Upon receiving a call from the manager accessing the reverse 9-1-1 feature, the onsite PBX server 104 plays back a verbal main menu message such as:

"This is the reverse 9-1-1 broadcast system. Press 1 to record a reverse 9-1-1 message, press 2 to listen to the currently recorded reverse 9-1-1 message, press 9 to activate the reverse 9-1-1 message."

Step 1200 of FIG. 12 corresponds to the situation when the manager presses 1 to record a reverse 9-1-1 message. The manager may preview the recorded message by pressing 2 and re-record it if necessary by pressing 1 again.

At step 1202, the onsite PBX server 104 determines whether the emergency broadcast has now been activated at the hotel. Continuing the above example, when the hotel manager presses 9 at the main menu to activate the reverse 9-1-1 message, control will proceed to step 1204; otherwise, control returns to step 1202.

At step 1204, the onsite PBX server 104 calls each room 112 at the hotel 102*a* in order to playback the emergency broadcast message recorded at step 1200. The reverse 911 feature allows the manager to send out a global announcement message that either rings or illuminates the message waiting lamp on the guess room phone (depending on the severity level set by the manager) that alerts all guests/admin of a critical situation. Likewise, if guests have stored the phone numbers of their personal mobile phones then the onsite PBX server 104 may also call these external phone numbers as well. A storage device within the onsite PBX server 104 stores a predetermined list of room extensions and possibly external phone numbers at which to play the reverse 9-1-1 broadcast message.

One of the numbers on the list may be 9-1-1 so that in the event an emergency occurs the manager can notify both the PSAP 150 and all the guests by recording and activating a single reverse 9-1-1 broadcast.

At step 1206, the onsite PBX server 104 tracks which rooms, guests, admin staff, and other of the pre-designated external phone numbers have listened to the emergency broadcast message. Statistics may be presented by the onsite PBX server 104 via a webpage admin console or verbally over the telephone menu at the same extension the manager called to setup the emergency broadcast. These statistics may be automatically passed by the onsite PBX server 104 to the cloud PBX server 120 for storage; in this way, police or other investigation personnel will still have access to this information even if the onsite PBX server 104 is destroyed or damaged during the emergency.

Figure 13:
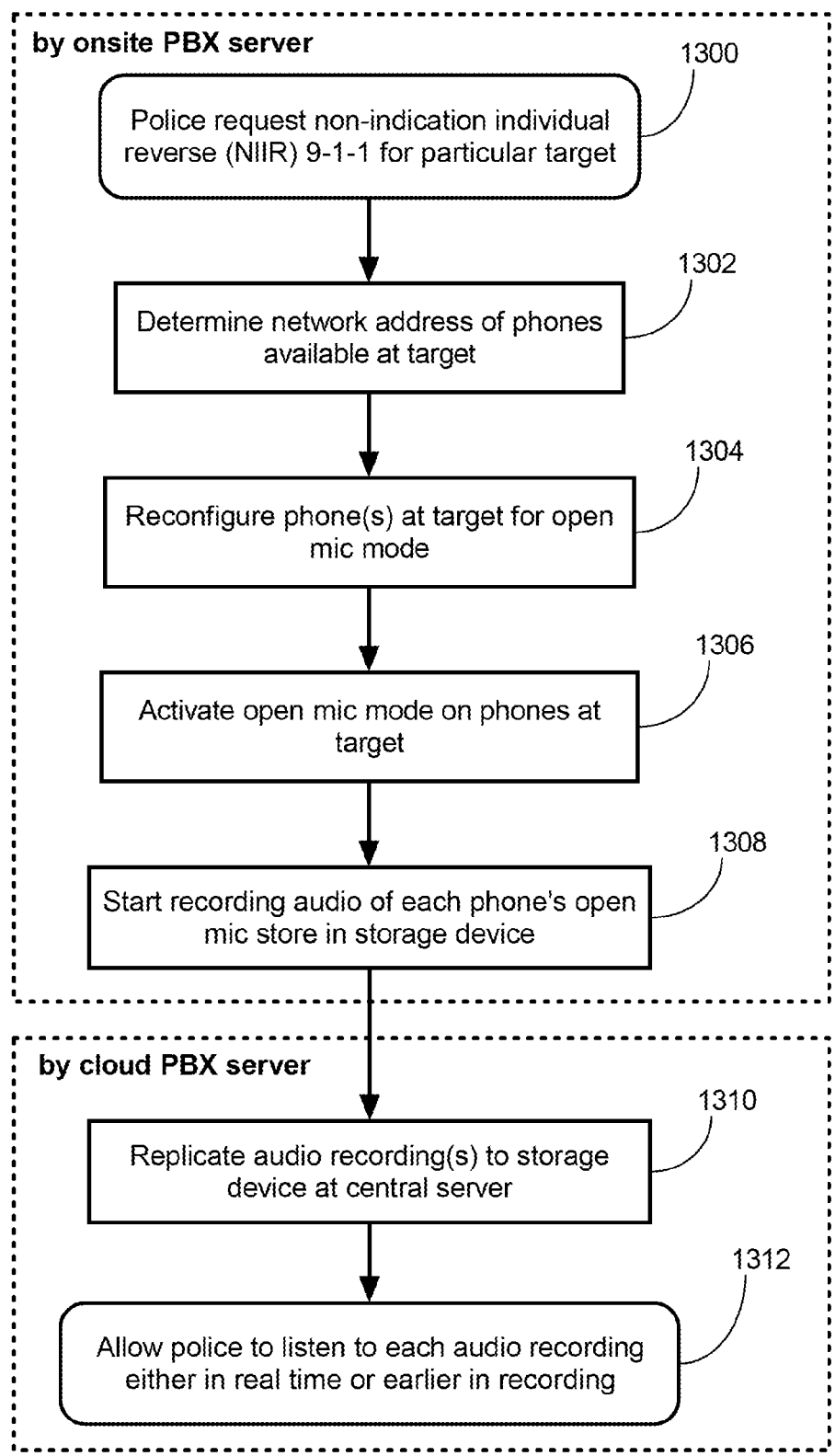
FIG. 13 is a flowchart describing a method of non-indication individual reverse (NIIR) 9-1-1 according to an exemplary embodiment of the invention.

FIG. 13 is a flowchart describing a method of non-indication individual reverse (NIIR) 9-1-1 according to an exemplary embodiment of the invention. NIIR 9-1-1 allows police or another authority to listen to what is happening in the vicinity of a target area or telephone number. For example, in the event there is a hostage situation in a hotel room 112a, with the correct access, the police are able to activate NIIR 9-1-1 for the target hotel room 112a and listen in to the room through the microphone on the in-room phone 108 and possibly the guest's own mobile phone 124 within that room 112a.

With reference to FIG. 1, the steps of FIG. 13 may be performed by the processors of the onsite PBX server 104 and the cloud PBX server 120 as indicated below. Alternatively, the steps may be performed by another device different than the device specified below. The steps of the flowchart are not restricted to the exact order shown, and, in other configurations, shown steps may be omitted or other intermediate steps added. In this embodiment, the system 100 operates as follows:

At step 1300, the onsite PBX server 104 receives a police request to turn on the NIIR 9-1-1 function for a target guest room 112a at the hotel 102a. In this example, the target guest room 112a is specified in the police request according to its room number. However, the target may also be a particular phone number such as the phone number of the mobile phone 124, which is known to be associated with the guest currently staying in the room 112. The police may determine the target according to any suitable method, for example, according to the source caller ID phone number on an incoming 9-1-1 call at the PSAP 150, a tip from a member of the public, verbally from a caller of an emergency call, hotel staff informing the PSAP operator that there is an illegal situation in that room, or by tracing a person's mobile phone 124 to a particular location via cell tower triangulation or GPS tracking.

In the following explanation, it will be assumed that there is a hostage situation occurring in guest room 112a and that the police are aware of the room number and request NIIR 9-1-1 of that room 112a to the onsite PBX server 104. The request may be received by the onsite PBX server 104 at step 1300 in any suitable manner. In one example, the police may be in verbal communication with the PBX vendor and the PBX vendor may remotely access the onsite PBX server 104 such as via secure shell (SSH) via the Internet 106 in order to input the request to the onsite PBX server 104.

At step 1302, the onsite PBX server 104 determines which phones are associated and/or available at the target to be monitored. For example, when the police request NII 9-1-1 for a target hotel room 112a, the onsite PBX server 104 will look-up in a database which in-room phones 108 are located in that target hotel room 112a. Additionally, the onsite PBX 104 may query the hotel PMS 114 and/or the hotel chain web server 109 in order to determine whether the guest currently registered for that room 112a has specified the phone number of their mobile phone 124. In the following example, it will be assumed that the onsite PBX server 104 determines the available phones at the target location to be: user's mobile phone 124 and in-room phone 108a shown in guest room 112a in FIG. 1.

The onsite PBX server 104 may further prevent any new calls being made to the in-room phone(s) 108a in the target guest room 112a. For example, in the event that a person outside the hotel attempts to call the target guest room 112a, this call will first be received by the onsite PBX server 104, which will either drop the call or connect it to another destination extension at the hotel because the NIIR 9-1-1 has already been requested for the phone 108a. When connecting the incoming call to another destination, the other destination extension may be a configurable option at either the onsite PBX server 104 or the cloud PBX server 120, for example, the police may request that any calls to the in-room phones 108a in the target location (room 112a in this example) be rerouted to the police rather than connected directly to the hostage takers in the room 112a.

At step 1304, the onsite PBX server 104 reconfigures the phones determined at step 1302 for "open mic" mode. In one configuration, the onsite PBX server 104 may send one or more command to in-room phone 108a via hotel LAN 110 to cause in-room phone 108a to behave as follows:

| Phone setting | New value | Result |
| --- | --- | --- |
| Audio ringer volume | 0 | Phone 108a will not ring or make any other noise when an incoming call is received, e.g., the phone 108a's ringer is now muted. |
| Visual ringer indicator | Off | Phone 108a will not flash any lights or make any other highly visual indications of when an incoming call is received. |
| Auto answer | On | Phone 108 will immediately answer all incoming calls; some phones may require a number of rings and this can be set to the lowest possible value such as to answer on the first ring. |
| Default answer mode | Speaker phone or conference mode | Phone 108 will by default use the speaker phone mode and will pick up all voice communications in the vicinity through its microphone and send this picked up audio to the caller (someone who calls that phone). |
| Speaker volume | Lowest level possible | Phone 108a will operate its speaker at the lowest possible volume setting. Muting the speaker would be the ideal setting if the phone supports muting the speaker while keeping its microphone on. |

The above settings may configured as a result of one or more commands sent directly from onsite PBX server 104 to each in-room phone 108 to be reconfigured. For example, some in-room phones 108 may accept on the fly reconfigurations for the above settings via hotel LAN 110.

Alternatively, in another embodiment, the onsite PBX server 104 may generate a new configuration image for each in-room phone 108a to be reconfigured. The new configuration images incorporate the above settings changes. The onsite PBX server 104 then loads the new configuration image in a phone server on hotel LAN 110. This may be the same server that the in-room phones 108 are pre-programmed to retrieve configuration images each time they are rebooted. In one configuration, the onsite PBX server 104 acts as the phone server itself. After loading a new configuration image for each phone 108 to be reconfigured for the NIIR 9-1-1 feature, the onsite PBX server 104 then sends a reboot command those in-room phones 108, which causes them to retrieve the new configuration images from the phone server and then apply the new settings.

After remotely reconfiguring the in-room phone 108a with these settings, the onsite PBX server 104 proceeds to step 1306 to activate NIIR 9-1-11 on each of the reconfigured in-room phones 108a by calling them.

At step 1306, the onsite PBX server 104 calls the in-room phone 108*a* that was reconfigured at step 1304. If the onsite PBX server 104 reconfigured multiple phones 108 at step 1304, then it will call each of the various in-room phones 108 that it reconfigured at step 1304. For example, the target location of interest to the police may be a hotel suite, which has different phones 108 in different rooms; in such a situation, the onsite PBX server 104 reconfigures all the phones 108 in the suite (or other target location) at step 1304 and then calls all the now reconfigured phones 108 at step 1306.

When making the call to the in-room phone(s) 108*a* in the target room 112*a*, the onsite PBX server 104 by default will mute the audio to the target phones 108 on the call. In other words, when the in-room phone 108 immediately answers the call and begins playing audio received on the call out of its speaker, there will be no audio to play because the onsite PBX server 104 is not providing any sound to the target phone 108. In this way, the people in the room may be entirely unaware that: 1) there has been an incoming call because phone 108*a* does not ring and does not flash any visual indicators, and 2) the call was automatically answered in speaker phone mode because there is no noise coming out of the phone's speaker after the call is answered.

At step 1308, the onsite PBX server 104 starts recording the audio it is receiving from each of the "open mic" phone(s) 108 that were activated at step 1306. The onsite PBX server 104 may store in audio storage device 115 a separate audio file for each "open mic" phone 108 that it is recording.

At step 1310, the onsite PBX server 104 sends the audio from the various "open mic" phones 108 to the cloud PBX server 120, which also stores the audio for each call in a central storage device such as a centrally located hard drive. One reason to replicate the audio of the calls for storage at the cloud PBX server 120 is to preserve evidence in the event that the onsite PBX server or local audio storage device 115 is damaged or destroyed during the ongoing incident. For example, if an explosive device is detonated and/or a fire occurs at hotel 102.

At step 1312, police are enabled to listen to each audio recording either in real time or afterwards. In one configuration, police are provided an access phone number and code from the PBX vendor. The police call the access phone number and the call is received at the cloud PBX server 120. The police then enter the access code using touch tone digits on their phone and gain access to a main menu which allows them to pick any "open mic" phones currently activated in order to listen to the audio. If there are multiple "open mic" phones, the cloud PBX server 120 may allow the police to join the audio together and listen to all "open mic" phones at the same. In this way, some parts of the conversation may be picked up better by some phones and the police will get a better understanding of the situation from multiple listening positions within the target location.

In another configuration, the cloud PBX server 120 provides a web-based UI interface to the police which displays the audio files for each "open mic" phone 108 as a waveform pattern and allow the police to select any part of any waveform pattern for playback. In this way, the police may visual see that there was audio activity on a particular "open mic" phone 108 at a particular time and then playback only that portion of interest.

In yet another configuration, the recorded audio for each "open mic" phone 108 may be played out of a separate speaker or headset allowing the police to focus on any that are of interest. Any other mechanism to enable the police to listen to the recorded audio information for the various "open mic" phones 108 may be utilized. For example, web-based API's or simply copying the audio files in a suitable format such as .WAV or .MP3 and providing these files to the police either via Internet 106 or a physical media such as a hard drive or flash drive.

In yet another configuration, rather than receiving audio information from the target phones, the onsite PBX server 104 may reconfigure the phone(s) at step 1304 in order to enable an "open video" mode. For example, the phones may include video cameras utilized during the conference mode to record video. At step 1304, the onsite PBX server 104 may configure the target phone(s) 108 to automatically turn on their cameras by default after they answer a call thereby enabling the police to see what is occurring in the room. Any settings that may alert the people in the vicinity of the phone to the fact that they phone is taking video may be disabled by the reconfigurations performed at step 1304. For example, if the phone has a screen, the onsite PBX server 104 may turn off the screen or set it to a lowest brightness. Additionally, when the onsite PBX server 104 calls the phone(s) at target 1306 in order to start receiving the video information, the onsite PBX server 104 may transmit a black screen to the phone(s) 108 so that it is less noticeable. Alternatively, the onsite PBX server 104 may transmit video that would appear to be a default screen on the phone such as a display showing an indication that no call is currently being made. The time/date or other default information usually display on the target phone such as its main menu may be sent as the video from the onsite PBX server 104 to the phone 108 while it is in "open video" mode. In this way, even upon inspection by a user of the phone 108, the screen will appear to indicate that nothing is happening and the user may not realize that the phone 108 is actually in a call and taking video and/or listening to audio.

Figure 14:
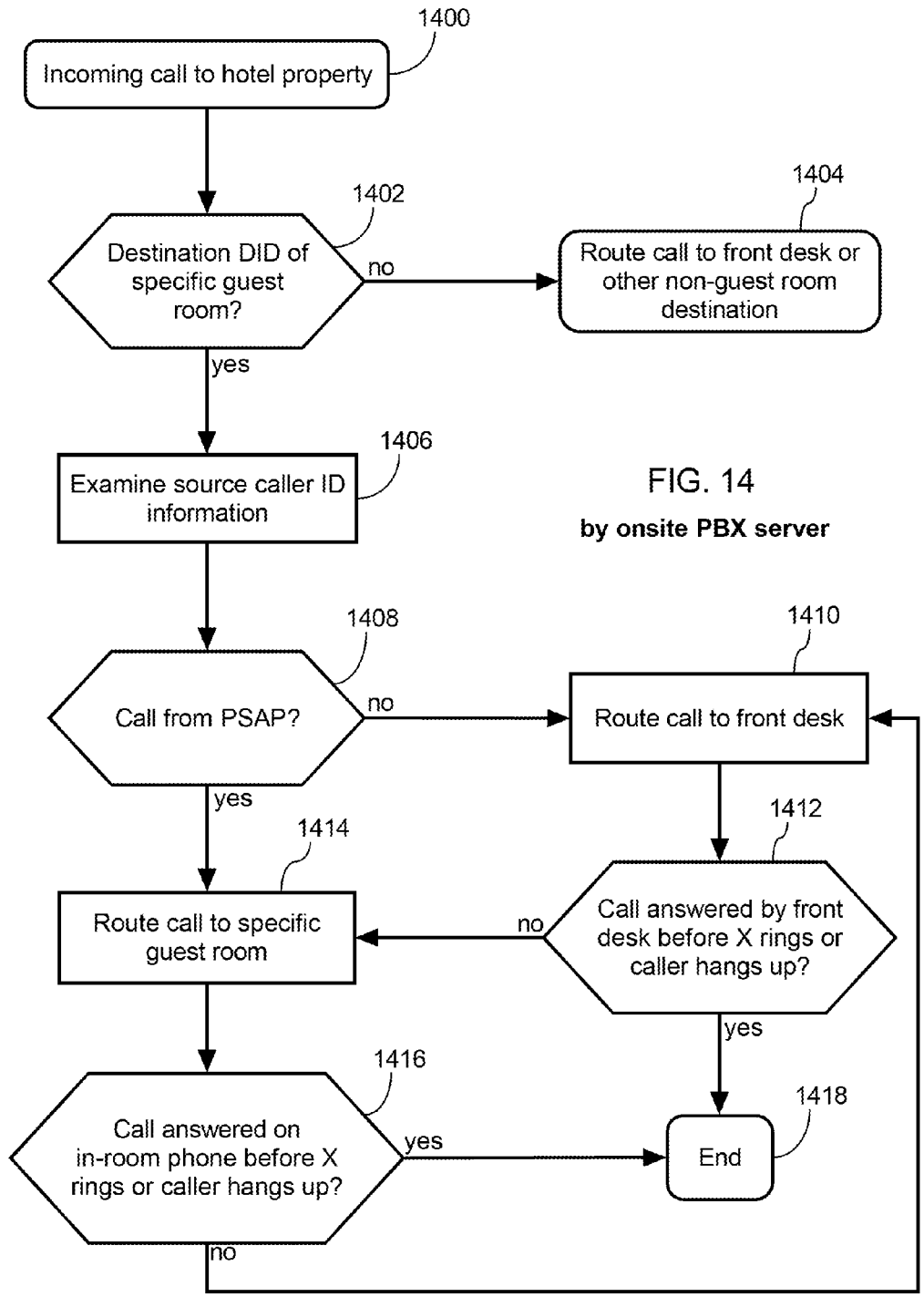
FIG. 14 is a flowchart describing a method of handling incoming calls at a hotel PBX according to an exemplary embodiment of the invention.

FIG. 14 is a flowchart describing a method of handling incoming calls at a hotel PBX according to an exemplary embodiment of the invention. With reference to FIG. 1, the steps of FIG. 14 may be performed by the processors of the onsite PBX server 104 as indicated below. Alternatively, the steps may be performed by another device different than the device specified below such as by the cloud PBX server 120. The steps of the flowchart are not restricted to the exact order shown, and, in other configurations, shown steps may be omitted or other intermediate steps added. In this embodiment, the system 100 operates as follows:

At step 1400, a call to the hotel 102 is received by the onsite PBX server 104. This step may be proceeded by the call arriving at the cloud PBX server 120 and then being passed to the onsite PBX server 104. In one example, the call may be from the PSAP 150 to the front desk or a specific guest room 112 at the hotel 102*a*; alternatively, the incoming call received at this step may be from a person trying to make a reservation at the hotel or the friend or coworker of a guest currently staying in one of the guest rooms 112.

At step 1402, the onsite PBX server 104 examines the destination phone number to determine whether the call is to a DID of a specific guest room 112 at the hotel 102*a*. In this configuration, each of the hotel guest rooms 112 has a dedicated phone number and the onsite PBX server 104 at this step determines whether the incoming call is destined to one of those dedicated numbers. If yes, control proceeds to step 1406; otherwise, control proceeds to step 1404.

At step 1404, because the destination DID of the incoming call is not a specific guest room 112, the onsite PBX server 104 routes the call to the front desk telephone extension at the hotel 102*a*. Alternatively, in another configuration, the call may be routed an auto-attendant voice menu system for the hotel 102a. In another configuration, the incoming call may have a DID associated with another non-guest room destination at the hotel such as front desk, VIP desk, room service, SPA center, etc. The onsite PBX server 104 routes the call to its specific non-guest room destination at this step 1404.

At step 1406, because the destination DID of the incoming call is a specific guest room 112 at the hotel 102a, the onsite PBX server 104 performs a further examination to check the source caller ID information of the incoming call. For example, the onsite PBX server 104 checks whether the source caller ID phone number matches 9-1-1 or another predetermined number utilized by PSAP 150.

At step 1408, in the event that the source caller ID phone number of the incoming call examined at step 1406 is 9-1-1 (or another predetermined number utilized by PSAP 150), control proceeds to step 1414. Alternatively, if the incoming call is not from 9-1-1, control proceeds to step 1410.

At step 1410, the onsite PBX server 104 routes the incoming call to the hotel front desk. When this step is reached from step 1408, it means the incoming call is not from the PSAP 150 and has a destination DID of a specific guest room 112. For example, the call may be from a friend, family member, or coworker of the guest staying in the specific guest room; alternatively, the call may be a misdialed call or telemarketing call. By routing all these calls to the front desk at step 1410, a hotel staff member may screen the call. If the caller does not know to which room they are trying to connect and/or does not know the name of the guest they are trying to reach, the front desk staff can refuse to connect the call to the room 112a indicated by the DID on the incoming call. In this way, guests are not bothered by undesirable calls. Alternatively, if the caller is trying to reach that specific room 112a or guest and front desk feel the call is legitimate, the front desk staff can connect the call to the room 112a. Rather than routing the call to front desk at this step 1410, another predetermined destination associated with the hotel 102 may be employed instead to vet the incoming call such as the auto-attendant system.

At step 1412, if the incoming call is not answered by the front desk staff before a predetermined number of rings X (e.g., 3 rings), the onsite PBX server 104 will forward the call directly to the guest room that is associated with the destination DID of the incoming call. The purpose of this step is to avoid dropping the call if the front desk are busy or otherwise unable to screen the incoming call. Usually the front desk will always be able to answer the call but in the event of an emergency where front desk cannot answer then rather than drop the call it is forwarded to the appropriate guest room 112.

At step 1414, the onsite PBX server 104 routes the incoming call to the specific guest room indicated by the destination DID of the incoming call. When this step is reached from step 1408, it means the incoming call is from the PSAP 150 and has a destination DID of a specific guest room 112. In this situation, rather than forwarding the incoming call to the hotel front desk for screening purposes, the call is immediately passed directly to the guest room 112 associated with the destination DID.

One reason is that E-911 requires a call back from the PSAP 150 if a 9-1-1 call is dropped before the PSAP operator receives all pertinent information. For example, a guest in guest room 112a may accidentally call 9-1-1 on the in-room phone 108a and then may hang up as soon as they realize their mistake. PSAP 150 receives the call and displays the source caller ID phone number and hotel name and address information to the PSAP operator handling the call. The caller's personal emergency information may also be displayed as per any of the above-described embodiments. However, as the caller immediately hung up without telling the PSAP operator of the reason for the call (i.e., that the call to 9-1-1 was actually a mistake), the PSAP operator will attempt to call back using the source caller ID phone number as seen at PSAP 150, i.e., the DID phone number associated with guest room 112a.

Therefore, when onsite PBX server 104 receives an incoming call with a destination DID of a specific guest room and a source caller ID of 9-1-1 (or another name/number utilized by PSAP 150), the onsite PBX server 104 simply connects the incoming call directly to the appropriate guest room 112a (step 1414). In this way, the least amount of the PSAP operator's time is wasted because the operator does not need to first talk to hotel front desk (or listen to the auto-attendant voice menu) before getting connected to the guest in room 108a in order to confirm that the 9-1-1 call was just a mistake. Furthermore, in the event that the 9-1-1 call was not a mistake but was inadvertently dropped, the PSAP operator is able to quickly reestablish contact with the guest experiencing the emergency without wasting time talking to front desk or listening to the auto-attendant voice menu.

At step 1416, if the incoming call is not answered by the guest staying in the guest room 112a before a predetermined number of rings X (e.g., 3 rings), the onsite PBX server 104 will forward the call to the front desk at the hotel 102a. The purpose of this step is to avoid dropping the call in the event that the guest is unable to answer the incoming call such as in the event they are incapacitated due to a medical emergency. For example, step 1416 may be reached due to the guest staying in the guest room 112 using in-room phone 108a to make a 9-1-1 call, the call is dropped before the PSAP operator is able to obtain any information from the caller, the PSAP operator therefore calls back and the call is recognized as from PSAP at step 1408 and routed to the specific guest room 112, but the guest does not answer the call back, i.e., does not answer in-room phone 108a before X (e.g., 3) rings. In the event that there really is an emergency in the room, the onsite PBX server 104 automatically routes the call to the hotel front desk. In this way, the PSAP operator will be able to discuss the situation with hotel front desk staff without having to look up the main desk phone number for the hotel or place another call.

Steps 1410, 1412, 1414, and 1416 form a loop that will continually cycle as long as the incoming call is not answered and the caller does not hang up. In this manner, if the incoming call is PSAP trying to call back to confirm why a 9-1-1 call was placed, the call will be initially routed by the onsite PBX server 104 to the guest's room from which the 9-1-1 call was originally placed (step 1408 to step 1414). However, if the guest does not answer the call, the onsite PBX server 104 will route the call to the front desk (step 1416 to step 1410). It is highly likely that front desk staff will answer the call, but in the event the staff is busy or cannot answer the call for whatever reason, the onsite PBX server 104 will route the call back to the guest room 112a from which the 9-1-1 call was originally placed (step 1412 to step 1414). In an example embodiment, this cycle will continue for as long as the caller does not hang up. In another embodiment, there may be a limit such as four cycles and then the onsite PBX server 104 will disconnect the call.

In an alternate embodiment, instead of step 1416 proceeding to step 1410 as shown in FIG. 14, step 1416 may modified to proceed to another step (not shown) where the incoming call is twinned to both the guest room 112a identified by the destination DID of the incoming call and the hotel's front desk. In other words, if the onsite PBX server 104 detects an incoming call from PSAP (at step 1408), the onsite PBX server 104 will route the call to the specific guest room 112a identified by the destination DID (step 1414). If the guest in that room does not answer the incoming call on in-room phone 108a by X rings (e.g., by 3 rings), the onsite PBX server will twin the call so that it continues ringing at the guest's room 112 and also rings at the front desk. In this way, the PSAP operator has a higher likelihood of the call being answered because both the in-room phone 108a in the specific guest room 112a and the front desk phone are continuously ringing.

At step 1418, if the call is answered (either at the front desk phone or the in-room phone 108a) then the caller and the answerer are able to communicate with each other as normal telephone call. Alternatively, if the caller hangs up before any answer occurs, the incoming call is dropped. In either case, the process ends without further routing of the incoming to a different extension. A log of the end result of the call may be stored by the onsite PBX server 104 to record the details of the call (e.g., destination DID, source caller ID info, time and date, etc.) and the actions taken (e.g., whether call was answered by in-room phone 108a or front desk and how many rings before answer, etc.)

FIG. 15 is a flowchart describing a method of handling incoming calls at a hospitality PBX according to another exemplary embodiment of the invention. With reference to FIG. 1, the steps of FIG. 15 may be performed by the processors of the onsite PBX server 104 as indicated below. Alternatively, the steps may be performed by another device different than the device specified below such as by the cloud PBX server 120. The steps of the flowchart are not restricted to the exact order shown, and, in other configurations, shown steps may be omitted or other intermediate steps added. In this embodiment, the system 100 operates as follows:

At step 1500, a call to the hotel 102a is received by the onsite PBX server 104. This step may be proceeded by the call arriving at the cloud PBX server 120 and then being passed to the onsite PBX server 104. In one example, the call may be from the PSAP 150 to the front desk or a specific guest room 112 at the hotel 102a; alternatively, the incoming call received at this step may be from a person trying to make a reservation at the hotel or the friend or coworker of a guest currently staying in one of the guest rooms 112.

At step 1502, the onsite PBX server 104 examines the destination phone number to determine whether the call is to a DID of a specific guest room 112 at the hotel 102a. In this configuration, each of the hotel guest rooms 112 has a dedicated phone number and the onsite PBX server 104 at this step determines whether the incoming call is destined to one of those dedicated numbers. If yes, control proceeds to step 1506; otherwise, control proceeds to step 1504.

At step 1504, because the destination DID of the incoming call is not a specific guest room 112, the onsite PBX server 104 routes the call to the front desk telephone extension at the hotel 102a. Alternatively, in another configuration, the call may be routed to an auto-attendant voice menu system or any other predetermined default destination for the hotel 102a. In another configuration, the incoming call may have a destination DID associated with another non-guest room destination at the hotel such as front desk, VIP desk, room service, SPA center, etc. The onsite PBX server 104 routes the call to its specific non-guest room destination at this step 1404.

At step 1506, the onsite PBX server 104 examines its log of previously placed calls to 9-1-1 (or another predetermined emergency number). In this embodiment, whenever one of the in-room phones 108 at the hotel is utilized to place an emergency call to 9-1-1, the onsite PBX server 104 stores a log of the call in a storage device within the onsite PBX server 104. This emergency call log records details of the emergency call such as time and date that the call was placed, time and date that the call ended (or duration of the call), the guest room 112 at the hotel from which the call was placed, the source telephone extension in the PBX system 100 from which the call was placed (e.g., the extension number of in-room phone 108a), etc. A purpose of examining the emergency call log at this step 1506 is to determine whether any outgoing emergency calls have been placed from the specific guest room identified at step 1502 within the last thirty minutes. (Any other suitable predetermined time duration may be utilized rather than thirty minutes in other embodiments.) In one example, this step 1506 may be performed by the onsite PBX server 104 searching the emergency call record to find any calls to 9-1-1 from the destination DID of the incoming call within the last 30 minutes.

At step 1508, when at least one outgoing call has been previously placed to 9-1-1 from the specific guest room associated with the destination DID of the incoming call within the last thirty minutes, control proceeds to step 1512; otherwise, control proceeds to step 1510. Again, the actual time duration utilized at this step 1508 may be programmable by hotel staff of the PBX vendor to allow the time duration to be different than thirty minutes.

At step 1510, the onsite PBX server 104 routes the incoming call to the hotel front desk. For example, the call may be from a friend, family member, or coworker of the guest staying in the specific guest room; alternatively, the call may be a misdialed call or telemarketing call. By routing all these calls to the front desk at step 1510, a hotel staff member may screen the call. If the caller does not know to which room they are trying to connect and/or does not know the name of the guest they are trying to reach, the front desk staff can refuse to connect the call to the room 112a indicated by the DID on the incoming call. In this way, guests are not bothered by undesirable calls. Alternatively, if the caller is trying to reach that specific room 112a or guest and front desk feel the call is legitimate, the front desk staff can manually authorize the onsite PBX server 104 to connect the call to the room 112a. Rather than routing the call to front desk at this step 1410, another predetermined destination associated with the hotel 102 may be employed instead to vet the incoming call such as the auto-attendant system.

At step 1512, the onsite PBX server 1512 checks its internal settings to determine whether the hotel has enabled "911 callback conference mode". For example, either the hotel staff or the PBX vendor may select a checkbox on a configuration screen when installing or reconfiguring the onsite PBX server 104 to enable 911 callback conferencing. When this feature is currently enabled at the hotel 102a, control proceeds to step 1516; otherwise, when the feature is disabled or otherwise not in use at hotel 102a, control proceeds to step 1514.

At step 1514, the onsite PBX server 104 routes the incoming call to the specific guest room as indicated by the destination DID of the incoming call. For example, if the DID of the incoming call is associated with hotel room 112*a*, the incoming call is routed by the onsite PBX server 104 to in-room phone 108*a* in hotel room 112*a*. Step 1514 is reached when the incoming call to the hotel received at step 1500 is destined for a specific guest room 112*a* at the hotel from which a call to 9-1-1 was recently placed (i.e., placed within the last 30 minutes in this example). In such a situation, rather than forwarding the incoming call to the hotel front desk for screening purposes, the call is immediately passed directly to the guest room 112 associated with the destination DID.

As explained above in the description of step 1414 for FIG. 14, one reason to directly re-route calls directly to the guest room is that E-911 requires a callback from the PSAP 150 if a 9-1-1 call is dropped before the PSAP operator receives all pertinent information. Please see the above description of step 1414 for various benefits of routing 9-1-1 callbacks directly to the guest room 112*a*.

At step 1516, the onsite PBX server 104 causes both the in-room phone 108*a* of the specific guest room 112*a* identified at step 1502 and the hotel's front desk phone to ring with an incoming call. In one configuration, this may be achieved by twinning the call to both those phone extensions so that the call may be answered on either; however, in preferred embodiment, even if the call is answered on one of the in-room phone 108*a* or the front desk phone, the other keeps ringing and may be answered afterwards.

The onsite PBX server 104 may first twin the call to both the in-room phone 108*a* extension and the front desk phone extension. Upon one of these phones answering the call, for example, upon the front desk answering, the onsite PBX server 104 passes voice traffic between the caller and the answerer (see step 1518). Further, the onsite PBX server 104 immediately initiates a new call to the other of the two extension so that it keeps ringing, for example, a new call to the in-room phone 108. Upon that $2^{nd}$ call being answered, the onsite PBX server 104 joins it into the first call so that all parties can hear and speak with each other (i.e., the onsite PBX server 104 creates a conference call)—see step 1518.

At step 1518, all parties that answer the incoming call are placed together in a conference call within the incoming caller and may converse. In other words, if the incoming call is to room "101", both the in-room phone 108 in room "101" and the phone at the hotel front desk will ring. If the call is first answered at the hotel front desk, the front desk staff will be connected to the incoming caller and the two may converse; however, the in-room phone 108 in room "101" continues to ring. In one embodiment, the continued ringing of the in-room phone 108 lasts for as long as at least one of the front desk and hotel staff are connected to the conference call. If both hang up, then the in-room phone 108 will stop ringing. Alternatively, a time limit may be placed on the in-room phone 108 so that it will only ring for 1 minute (or another predetermined time duration) after the call is first answered by the front desk. On the other hand, if the guest first answers in-room phone 108*a*, they will be connected with the incoming caller but the front desk phone will continue to ring in a similar manner. All parties that answer are joined together in a conference call with the caller.

An example of a beneficial usage scenario of the method of FIG. 15 is as follows: A guest staying in guest room 112*a* experiences a medical emergency and calls 9-1-1 from their in-room phone 108*a*. The onsite PBX server 104 and/or cloud PBX server 120 forward the call to PSAP 150 through any of the previously described mechanism including routing the call directly through the backup trunking 113.

The PSAP operator handing the call at a minimum will see the source caller ID of the incoming call being the DID of guest room 112*a*, for example, "614-582-6514". (The PSAP operator may also see other information such as the name of the hotel, the address of the hotel, the guest room number of room 112*a*, and/or the emergency information of the guest making the call according to which of the above-described features are enabled or in use.)

Continuing the example, perhaps in a panic, the guest in room 112*a* hangs up the call before speaking to the PSAP operator. Alternatively, the PSAP operator may need to ask more questions after the call was deliberately ended by either party. To reestablish communications with the guest, the PSAP operator calls back the DID of the guest room 112*a*'s in-room phone 108, e.g., "614-582-6514" in this example.

As a result of the callback to "614-582-6514" from the PSAP operator, the flowchart of FIG. 15 proceeds from step 1500 to step 1512 as previously described.

If the hotel has not enabled or has chosen to not implement "911 callback conference mode", step 1512 proceeds via the "no" branch to step 1514 and the onsite PBX server 104 routes the incoming call directly to the in-room phone 108*a* in the guest's room 112*a*. The PSAP operator may now communicate with the guest and obtain any necessary information. Beneficially, because a 9-1-1 call was recently placed from the destination phone number of the incoming call (i.e., the DID of the specific guest room 112*a* identified at step 1502), the callback to this guest room 112*a* from the PSAP operator is not rerouted to the front desk for screening by front desk staff like a non-emergency call would be at step 1510.

Alternatively, assuming the "911 callback conference mode" is enabled, step 1512 proceeds via the "yes" branch to steps 1516 and 1518 causing both the front desk phone and the in-room phone 108*a* to ring. Assuming both the front desk staff and the guest in room 112*a* answer the incoming call on their respective phones, both are placed in a conference call with the PSAP operator (the originating caller in this example). While the three parties are on the conference call, if the guest's medical emergency worsens and the guest is unable to speak, front desk or other hotel staff may run to the guest's room 112*a* and perform emergency first aid (e.g., CPR, artificial respiration, choking rescue, etc.) while EMS is dispatched by the PSAP operator. Beneficially, hotel staff are able to assist the PSAP operator with any 9-1-1 callbacks including helping the PSAP operator determine the severity of the situation and assess the EMS dispatch requirements.

After thirty minutes (programmable time duration) have passed since 9-1-1 was dialed from the in-room phone 108*a* in guest room 112*a*, if another incoming call is received (at step 1500) and has the DID (e.g., "614-582-6514") of that specific guest room 112*a* ("yes" branch of step 1502), the result of step 1508 will be the "no" branch and the onsite PBX server 1510 routes the call to the designated default answering point (e.g., menu, voice prompt, front desk, voicemail, etc.) The default answering points at step 1504 and 1510 may also be programmable options and change according to time of day etc.

Other variations of the method described in FIG. 15 are also possible, for example, a new step similar to step 1408 in FIG. 14 can be inserted between steps 1508 and 1512 to check whether the incoming call is actually from the PSAP operator. This may be beneficial to avoid routing non-emergency calls directly to the guest room (and possible conferenced with the front desk) if a 9-1-1 call was recently placed from the guest room 112*a*. For example, the new step inserted may check to see if the incoming caller ID is "911" or another predetermined emergency number; if yes, control proceeds to step 1512 and the rest of the steps of FIG. 15 are as previously described. Alternatively, if the incoming call is not from 9-1-1 (e.g., the incoming may be a telemarketing call that just happened to be within thirty minutes of a 9-1-1 being placed from that room 112*a*), control proceeds to step 1510 to route the call to the front desk for screening purposes.

In another variation, a new step similar to step 1416 in FIG. 14 may be added after step 1514 to catch the situation where the guest does not answer the call back from the PSAP. In other words, after step 1514, if the call is not answered on in-room phone 108 by X rings (e.g., four rings), the onsite PBX server 104 will: a) reroute, b) twin, and/or c) conference the incoming call to the front desk phone so that hotel staff may answer and discuss the situation with the PSAP operator.

In an exemplary embodiment of the invention, users store information that would be relevant to police, fire, and other first responders in the event of an emergency. Each user's personal emergency information is stored associated with the user's unique identifier in a database. When the user later places an emergency call, the user's emergency information is automatically made available to the public-safety answering point operator handling the call. For example, the user identifier of a guest currently checked in to a hotel room from which a 9-1-1 call is placed is passed to a PSAP controller, which then queries the database and obtains the caller's emergency information associated with that user identifier. Key hotel personal are notified of the call and may listen to and break in to the ongoing call in order to assist. A reverse 9-1-1 broadcast feature enables hotel personnel to quickly notify guests of an emergency situation on both in-room and mobile phones. In the event that police need to conduct surveillance on a target location, the onsite PBX server reconfigures phones within the vicinity of the target location to operate in an "open mic" or "open video" mode and records the audio/visual information received. An incoming call to a specific hotel room that is from the PSAP is automatically connected to the in-room phone in that room even if other incoming calls not from the PSAP are being screened by front desk. In the event that the PSAP's call to the guest room is not answered, the call may be rerouted or twinned so that it rings at the front desk. Alternatively, incoming calls to a specific hotel room from which 9-1-1 has recently been called may be either directly passed to the that room's in-room phone or placed in a conference call with both that room's in-room phone and the front desk staff at the hotel; whereas incoming calls to other hotel rooms from which 9-1-1 has not recently been called are passed only to the front desk or another programmable answering point for screening purposes.

Although the invention has been described in connection with preferred embodiments, it should be understood that various modifications, additions and alterations may be made to the invention by one skilled in the art without departing from the spirit and scope of the invention as defined in the appended claims. For example, in another configuration of the invention, one or more of the various functions of the onsite PBX server 104, the cloud PBX server 120, AEI controller, PSAP controller 156, or any other device described above or shown in the figures may be implemented as another device such as a another computer having its own processor(s), network interface(s), storage medium/media, and other hardware necessary components.

In the above description, the exemplary user indication of "guest" is utilized to refer to users as it common for customers of a hospitality establishment to be referred to as guests. However, it is not a requirement that users must be customers of the hospitality establishment and the term "guest" in this description includes other users such as current guests in the hotel, people who are attending a conference or meeting in the hotel, staff members at the hotel, or any other person or user who may need or want to access a network service over a computer network at the hospitality establishment. Future guests that have reservations, potential future guests that don't yet have reservations, and other users may also be enabled to setup personal emergency information in a similar manner. For example, a demonstration of the technology may be available in a hotel lobby guest area and all users would be able to try out the system 100.

Additionally, it is not necessary that the users bring their own mobile phone 124. In another configuration, one or more of the mobile phones 124 may be provided to the user by the hotel. It should also be noted that although portable phones that are easily carried are anticipated by the inventors as being particularly useful as the mobile phone 124, it is not a strict requirement that the mobile phone 124 be easily carried. Other larger devices capable of making phone calls such as phones integrated with computers or other electronic equipment capable of being moved may also act as mobile phone 124 in conjunction with the invention. Different mobile phone 124 communication standards such as GSM, CDMA, analog etc. may also be utilized in conjunction with the invention.

Although the invention has been described as being utilized at a hotel for illustration purposes, the present invention is equally applicable to any hospitality related location or service wishing to provide enhanced safety information for emergency calls including but not limited to hotels, motels, resorts, hospitals, apartment/townhouse complexes, restaurants, retirement centers, cruise ships, busses, airlines, airports, shopping centers, passenger trains, libraries, coffee shops, hotspots, etc. Additionally, the invention is applicable outside of the hospitality industry to provide emergency information from mobile phones, residential phones, business phones and other usages in addition to the above-described hospitality examples.

Although the invention has been described focusing on emergency telephone calls, the invention is also applicable to other types of emergency calls such as those made using both audio/visual calls signals, text messages such as SMS and MMS, and other alert signals that may sent by a caller and received at a PSAP 150 or other monitoring destination in the event of an emergency.

Although the invention has been described focusing on providing personal emergency information to PSAP, the invention may be employed to make any information available to PSAP (or another destination) including non-personal and non-emergency information. For example, a tour group may be travelling together and the emergency information for each user in the group may be the same and include their tour guide's contact details and/or the tour company's contact details. In another example, the process of FIG. 9 may be utilized to deliver any information to key personnel at the hotel 102*a* and is not limited to only delivering emergency information. For example, a VIP guest may have text-based notes describing their guest preferences and this information may be sent in a manner similar to FIG. 9 whenever the guest calls room service.

Although the invention has been described utilizing 9-1-1 as the emergency number utilized in the above examples, the invention may also be employed with another predetermined emergency number instead such as 1-1-2 (Europe) 1-1-9 (Taiwan), for example.

The various separate configurations, elements, features, embodiment, and modules of the invention described above may be integrated or combined. One or more processors may operate pursuant to instructions stored on a tangible, non-transitory computer-readable medium to perform the above-described functions. Examples of the computer-readable medium include optical media (e.g., CD-ROM, DVD discs), magnetic media (e.g., hard drives, diskettes), and other electronically readable media such as flash storage devices and memory devices (e.g., RAM, ROM). The computer-readable medium may be local to the computer executing the instructions, or may be remote to this computer such as when coupled to the computer via a computer network such as the Internet 106. The one or more processors may be included in a general-purpose or specific-purpose computer that becomes a special purpose machine performing the above-described functions as a result of executing the instructions. In another example, rather than being software modules executed by one or more processors, the various modules and described functionality, such as actions performed by the onsite PBX server 104, the cloud PBX server 120, the AEI controller 147, the PSAP controller 156, the ALI controller 157, the user's mobile phone 124, and telecom servers within telecom phone network 118, may be implemented as hardware modules configured to perform the above-described functions. Functions of single modules and devices as described may be separated into multiple units, or the functions of multiple modules and devices may be combined into a single unit. Unless otherwise specified, features described may be implemented in hardware or software according to different design requirements. In addition to a dedicated physical computing device, the word "server" may also mean a service daemon on a single computer, virtual computer, or shared physical computer or computers, for example. Additionally, all combinations and permutations of the above described features and configurations may be utilized in conjunction with the invention.

What is claimed is:

1. A system for providing personalized emergency information to a public-safety answering point (PSAP) regarding a guest of a hospitality establishment, the system comprising:
   a server configured to receive emergency information from a plurality of different users;
   a storage device configured to store each of the users' emergency information associated with a respective unique user identifier; and
   a controller configured to determine a particular user identifier, the particular user identifier corresponding to a user who is currently checked in to a guest room in the hospitality establishment at the time an emergency call is placed from the guest room;
   wherein the controller is further configured to send to the Public Safety Answering Point (PSAP) the emergency information associated with the particular user identifier.

2. The system of claim 1, wherein the controller is configured to determine the particular user identifier by receiving identification information from PSAP and correlating that identification information with a particular user identifier.

3. The system of claim 2, wherein:
   the identification information is a phone number of a guest room at the hotel; and
   the controller is further configured to query a property management system of the hotel in order to look up the particular identifier of the user currently checked in to the guest room that corresponds to the phone number.

4. The system of claim 2, wherein the identification information received from the PSAP is the particular user identifier.

5. The system of claim 1, wherein the controller is further configured to determine the particular user identifier by:
   detecting the emergency call being placed from the guest room; and
   querying a property management system of the hotel in order to look up the particular identifier of the user currently checked in to the guest room in response to detecting the emergency call.

6. The system of claim 1, wherein the controller is configured to send the emergency information associated with the particular user identifier to the PSAP by:
   detecting when the emergency call is made from the guest room;
   adding the particular user identifier to the caller ID information of the emergency call when forwarding the emergency call to the PSAP;
   receiving a query for the emergency information associated with the user identifier from the PSAP; and
   sending to the PSAP in response to the query the emergency information for the user identifier.

7. The system of claim 1, wherein the controller is configured to send the emergency information associated with the particular user identifier to the PSAP by:
   detecting when the emergency call is made from the guest room;
   adding a tag to the caller ID information of the emergency call when forwarding the emergency call to the PSAP, the tag being correlated to the particular user identifier of the guest room;
   receiving a query for the emergency information associated with the tag from the PSAP; and
   sending to the PSAP in response to the query the emergency information for the particular user identifier associated with the tag.

8. The system of claim 1, wherein the controller is configured to send the emergency information associated with the particular user identifier to the PSAP by:
   detecting when the emergency call is made from the guest room; and
   sending the emergency information associated with the user identifier of the particular guest correlated with the guest room to the PSAP via e-mail, short message service (SMS), multimedia message service (MMS), or another electronic communication.

9. The system of claim 1, wherein the controller is configured to send the emergency information associated with the particular user identifier to the PSAP by:
   receiving a query from the PSAP requesting the emergency information associated with the phone number of the guest room from which the emergency call was placed; and
   sending the emergency information associated with the particular user identifier that is currently correlated with the guest room identified in the query.

10. The system of claim 1, wherein the emergency information associated with the particular user identifier specifies a medical condition, disease, or required treatment of the user who is currently checked in to a guest room in the hospitality establishment at the time the emergency call is placed from the guest room.

11. The system of claim 1, wherein the emergency information associated with the particular user identifier specifies the user's allergies to medication.

12. The system of claim 1, wherein the emergency information associated with the particular user identifier specifies contact information of another person acting as an emergency contact in the event the user experiences a medical problem.

13. The system of claim 1, wherein the controller is configured to send the emergency information associated with the particular user identifier to the PSAP by:

sending the emergency information associated with the particular user identifier when the emergency call is made to the PSAP from the guest room.

* * * * *